(12) United States Patent
Malik et al.

(10) Patent No.: US 7,005,124 B2
(45) Date of Patent: Feb. 28, 2006

(54) DENDRITIC-ANTINEOPLASTIC DRUG DELIVERY SYSTEM

(75) Inventors: Navid Malik, London (GB); Ruth Duncan, London (GB); Donald A. Tomalia, Midland, MI (US); Roseita Esfand, Mt. Pleasant, MI (US)

(73) Assignee: Dendritic Nanotechnologies, Inc., Mt. Pleasant, MI (US)

( * ) Notice: Subject to any disclaimer, the term of this patent is extended or adjusted under 35 U.S.C. 154(b) by 340 days.

(21) Appl. No.: 10/016,733

(22) Filed: Oct. 29, 2001
(Under 37 CFR 1.47)

(65) Prior Publication Data

US 2003/0064050 A1 Apr. 3, 2003

Related U.S. Application Data

(60) Continuation-in-part of application No. 09/881,126, filed on Jun. 14, 2001, now Pat. No. 6,790,437, which is a division of application No. 09/111,232, filed on Jul. 7, 1998, now Pat. No. 6,585,956.

(60) Provisional application No. 60/051,800, filed on Jul. 7, 1997.

(51) Int. Cl.
*A61K 47/48* (2006.01)
*A61K 33/24* (2006.01)
*A61K 31/80* (2006.01)

(52) U.S. Cl. .............................. 424/78.17; 424/78.21; 424/DIG. 16

(58) Field of Classification Search ............. 424/78.17, 424/DIG. 16, 78.27; 525/540
See application file for complete search history.

(56) References Cited

OTHER PUBLICATIONS

Esfand, et al., "Poly(amidoamine) (PAMAM) Dendrimers: from Biomimicry to Drug Delivery and Biomedical Applications", DDT vol. 6, No. 8, pp. 427-436 (Apr. 2001).
Malik, et al., "Dendrimer-Platinate: A Novel Approach to Cancer Chemotherapy", Anti-Cancer Drugs, 10, pp. 767-776 (1999).
Ohndorf, et al., "Basis for Recognition of Cisplatin-Modified DNA by High-Mobility-Group Proteins", Letters to Nature, vol. 299, pp. 708-712, (Jun. 1999).

*Primary Examiner*—Edward J. Webman
(74) *Attorney, Agent, or Firm*—Karen L. Kimble

(57) ABSTRACT

Antineoplastic dendritic polymer conjugates which are useful drug delivery systems for carrying antineoplastic agents to malignant tumors are prepared by obtaining a dendritic polymer having functional groups which are accessible to an antineoplastic agent capable of interacting with the functional groups, and contacting the dendritic polymer with the antineoplastic agent. The preferred platin-based analogues of the antineoplastic agents conjugated to the dendritic polymer may be administered intravenously, orally, parentally, subcutaneously, intramuscularly, intraarterially or topically to an animal having a malignant tumor in an amount which is effective to inhibit growth of the malignant tumor. The antineoplastic dendritic polymer conjugates exhibit high drug efficiency, high drug carrying capacity, good water solubility, good stability on storage, reduced toxicity, and improved anti-tumor activity in vivo.

7 Claims, 18 Drawing Sheets

Effect of Cisplatin and Dendrimer (3.5) Conjugate on Cor L23 cells in Vitro

Effect of Cationic Dendrimers on Haemolysis of rat erythrocytes, 1h

Effect of Anionic Dendrimers on Haemolysis of rat erythrocytes, 1h

Effect of Anionic Dendrimers on B16F10, 72h

- △ dextran
- ● Gen 1.5
- ■ Gen 2.5
- □ Gen 3.5
- ▲ Gen 7.5
- ○ poly-L-lysine

Effect of Cationic Dendrimers on B16F10, 72h

- △ dextran
- ● Gen 1
- ▲ Gen 3
- ■ Gen 4
- ○ poly-L-lysine

Effect of Cationic Dendrimers on CCRF-CEM, 72h

- △ dextran
- ● Gen 1
- ▲ Gen 3
- ■ Gen 4
- ● poly-L-lysine

Effect of Anionic Dendrimers on CCRF-CEM, 72h

- △ dextran
- ● Gen 1.5
- ■ Gen 2.5
- □ Gen 3.5
- ▲ Gen 7.5
- ● poly-L-lysine

Effect of Anionic Dendrimers on HepG2, 72h

- △ dextran
- ● Gen 1.5
- ■ Gen 2.5
- □ Gen 3.5
- ▲ Gen 7.5
- ○ poly-L-lysine

Effect of Cationic Dendrimers on HepG2, 72h

- ● Gen 1
- △ dextran
- ■ Gen 4
- ▲ Gen 3
- ○ poly-L-lysine

Chloride Release from Cisplatin in Water and during reaction of Cisplatin to Gen 3.5

—●— + gen 3.5
—▲— cisplatin alone

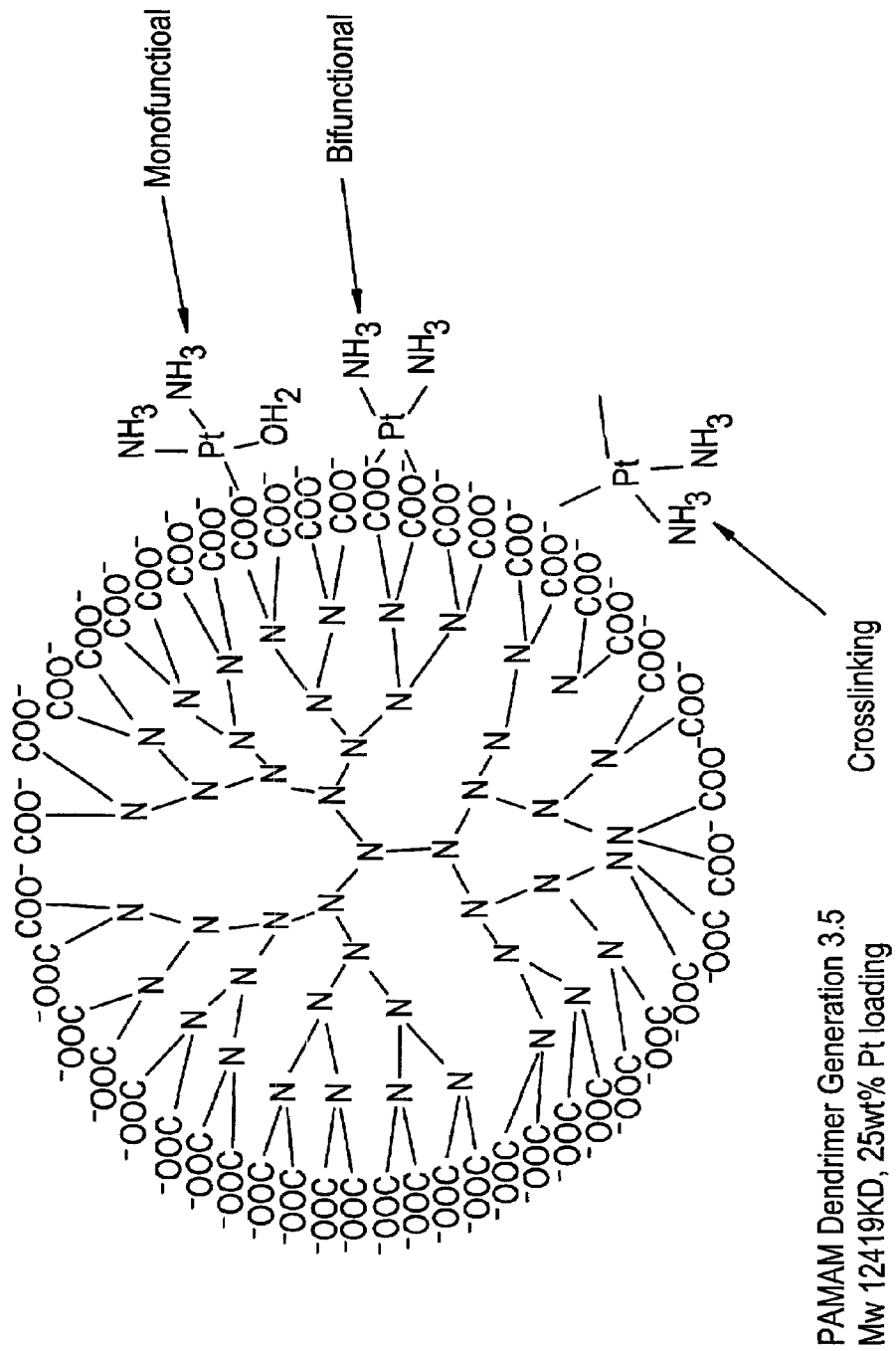

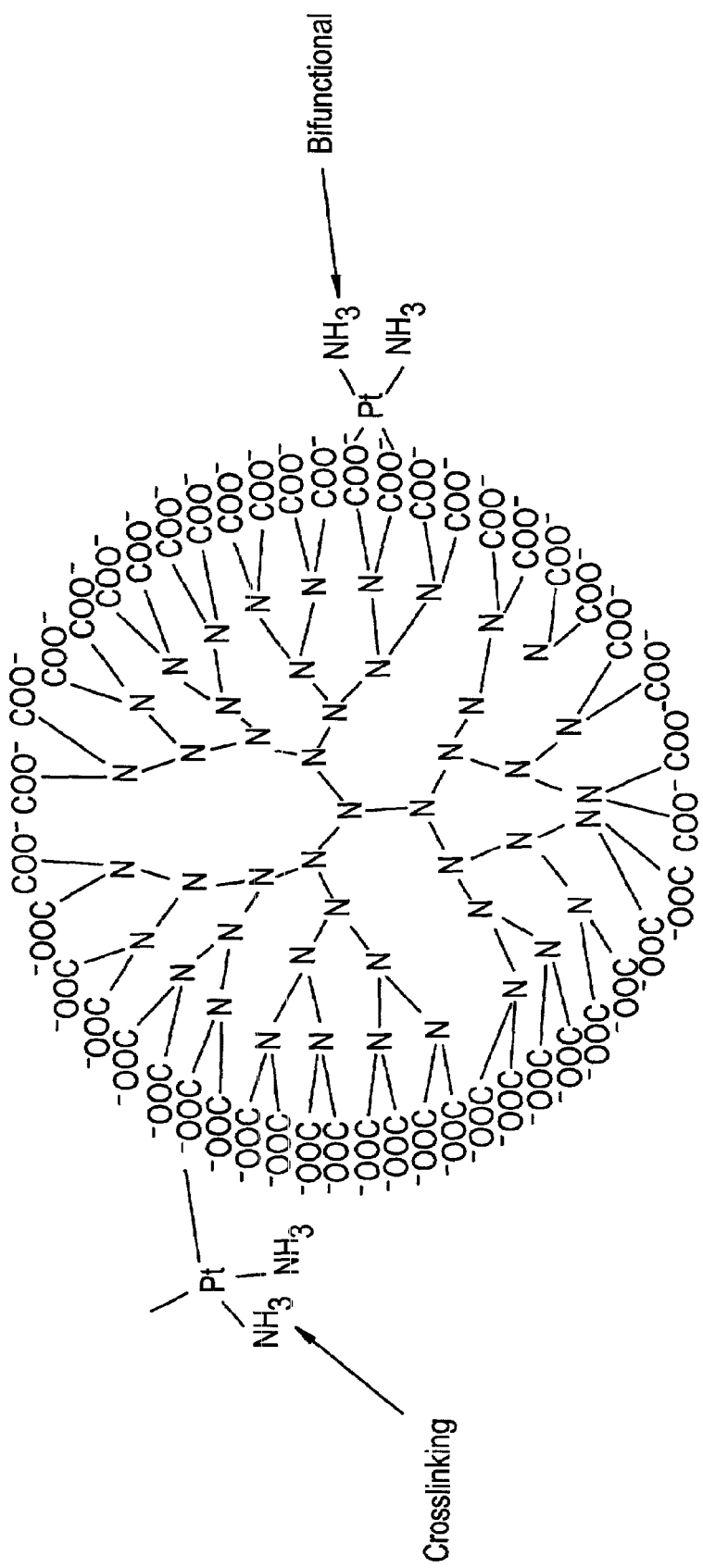

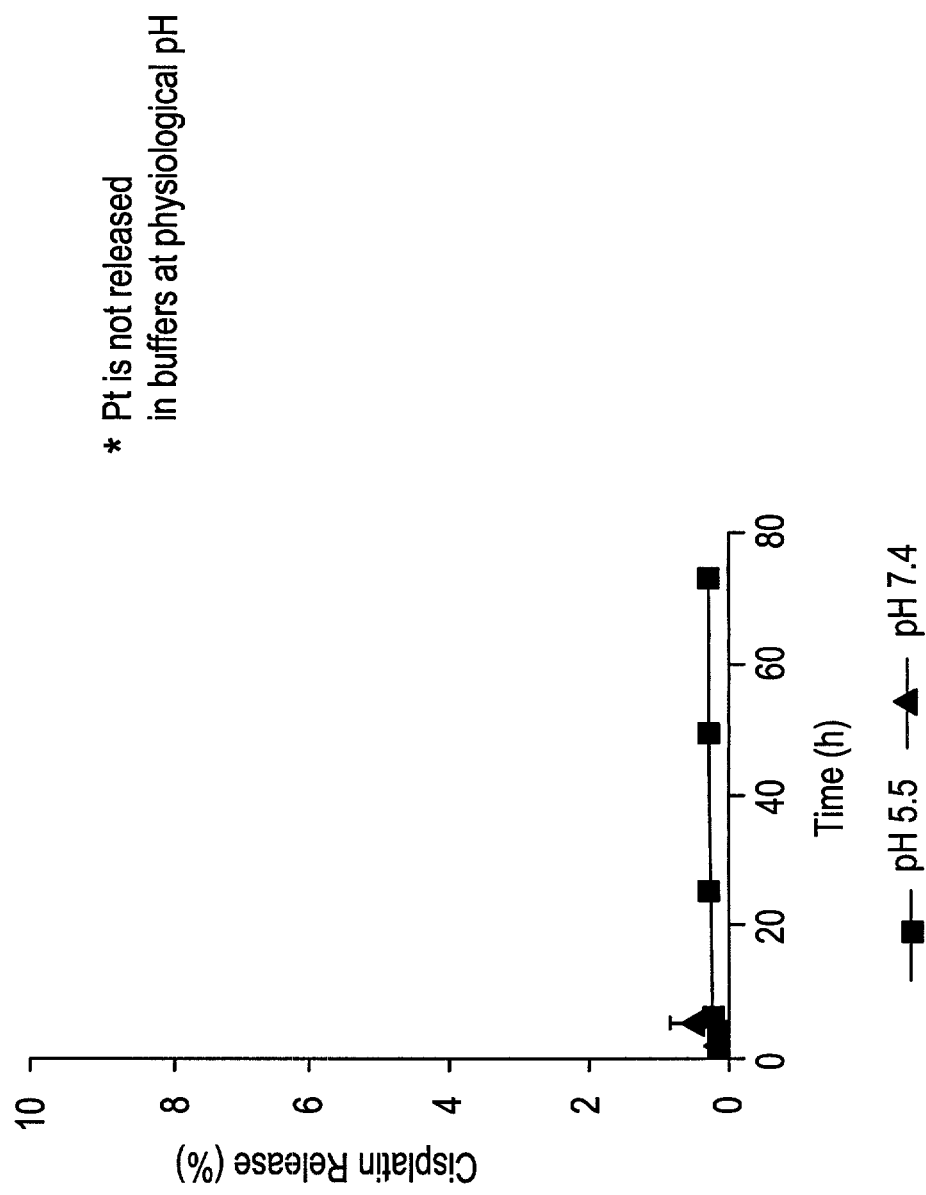

Effect of Cisplatin and Dendrimer (3.5) Conjugate on Cor L23 cells in Vitro

○ cisplatin    ■ dendrimer conjugate

Effect of Dendrimer-Pt on Established B16 melanoma

Accumulation of dendrimer-plantinum and platinum injected i.v. in C57 mice bearing B16F10 s.c. tumour (by AAS)

Effect of Dendrimer (gen 3.5) on the body weight of DBA2 mice bearing L1210 leukaemia Tumour

- Cisplatin 1 mg/kg
- Dendrimer-Pt 1 mg/kg
- Dendrimer-Pt 15 mg/kg

Liver

- Cisplatin 1 mg/kg
- Dendrimer-Pt 1 mg/kg
- Dendrimer-Pt 15 mg/kg

DENDRITIC-ANTINEOPLASTIC DRUG DELIVERY SYSTEM

CROSS REFERENCE TO RELATED APPLICATIONS

This is a continuation-in-part of U.S. Ser. No. 09/881,126, filed Jun. 14, 2001, now U.S. Pat. No. 6,790,437 allowed, which is a divisional of U.S. Ser. No. 09/111,232, filed Jul. 7, 1998, now issued as U.S. Pat. No. 6,585,956, which claims benefit of U.S. Provisional Application No. 60/051,800, filed Jul. 7, 1997, now abandoned, all of which are incorporated herein by reference.

FIELD OF THE INVENTION

This invention relates to the treatment of cancer in animals, especially humans, using dendritic polymer conjugates having an antineoplastic drug present.

BACKGROUND OF THE INVENTION

The use of polymers as carriers for drugs, especially those drugs that have low water solubility at physiological pH, are toxic to the normal tissue, or cannot be administered in sufficient dosage, has gained interest in recent years [e.g., H. Ringsdorf, *J. Polymer Sci.*: Symp. 51, 135–153 (1975)]. A polymer carrier for antineoplastic drugs would provide a useful system for administration of these drugs because of their solubility, toxic and higher dose at delivery characteristics. Several efforts to deliver doxorubicin are illustrative of this effort [e.g., R. Duncan et al., "Preclinical Toxicology of a Novel Polymeric Antitumor Agent: I-copolymer-doxorubicin (PK1)", *Hum. Exp. Toxiocol.* 17(2), 93–104 (1998); P. A. Vassey et al., "Phase I Clinical and Pharmacokietic Study of PK1 [N-(2-Hydroxypropyl)methacrylamide Copolymer Doxorubicin]: First Member of a New Class of Chemotherapeutic Agents—Drug-Polymer Conjugates", *Clin. Cancer Res.* 5, 83–94 (1999); L. W. Seymour et al., "N-(2-Hydroxypropyl)methacrylamide Copolymers Targeted to the Hepatocyte Galactose-receptor; Pharmacokinetics in DBA$_2$ Mice", *Br. J. Cancer* 63, 859–866 (1991);

The prospect of using dendritic polymers as caters or carriers for drug delivery has been previously proposed on account of the unique structure and characteristics of these polymer molecules [R. Esfand and D. A. Tomalia, "Poly (amidoamine) (PAMAM) Dendrimers: from Biorimicry to Drug Delivery and Biomedical Applications", research focus, DDT 6(8), 427–436 (Apr. 8, 2001); U.S. Pat. Nos. 5,338,532 and 5,527,524]. More specifically, it has been proposed that the external surface functionality and interior morphological characteristics of dendritic polymer molecules appear to be very promising for developing new methods for controlling drug release and targeted drug delivery systems. However, relatively little work has been done in specific areas of drug delivery. In particular, the use of dendritic polymers as effective caters for specific anti-tumor agents has not heretofore been demonstrated.

Certain platinum containing compounds, particularly carboplatin (cis-diamine(1,1-cylobutanedicarboxylato)platinum (II)) and cisplatin (cis-diamminedichloroplatinum) have been used in the treatment of ovarian cancer, lung cancer, testicular cancer, breast cancer, stomach cancer and lymphoma. However, because of the non-specific toxicity and poor water solubility of these platinum-containing compounds, the use of carboplatin and cisplatin has been relatively limited.

In order to overcome the non-specific toxicity and water solubility problems associated with cisplatin and carboplatin, it has been proposed to use linear polymers as carriers for these drugs. However, the use of linear polymers as caters in drug delivery systems has several disadvantages. A major disadvantage with linear polymer drug carriers is that they are heterogenous, polydisperse compositions containing various different molecular weight polymer molecules with a limited number of functional groups and/or reactive sites. Because linear polymer compositions are not comprised of molecules having a precisely defined structure, it is more difficult to maintain uniform polymer properties, drug delivery properties, and therapeutic efficacy. As a result it is relatively difficult to obtain regulatory (e.g., FDA) approval of the linear polymer-drug composites. Another disadvantage with the use of linear polymers as drug-carriers is that the location, and hence the availability, of the drug is difficult to control. In particular, the drug must either be bound covalently or non-covalently in a random unpredictable manner and the linear polymer structure lacks well-defined cargo space for the drug. The tendency of the drug to become buried in the linear polymer leads to greater unpredictability on account of the non-uniform or heterogeneous properties of the linear polymer molecules, and results in reduced drug efficiency because a significant proportion of the drug molecules are not effectively presented to the cell being treated. In some cases the random coil structure of the linear polymers may even prevent successful drug attachment within the coil and lead to passive entrapment, leading to uncontrolled drug release (e.g., random diffuse system), i.e., lack of uniformity in the timing of the drug release.

Accordingly, it would be highly desirable to provide a precisely defined drug delivery system for cisplatin and carboplatin, as well as related antineoplastic agents, which exhibit high drug efficiency, high drug carrying capacity, good water solubility, good stability on storage, reduced toxicity, and improved anti-tumor activity in vivo.

U.S. Pat. No. 5,338,532 teaches polymer conjugates comprising dense star polymers associated with a carried material, the disclosure of which is hereby incorporated by reference. [One type of dense star polymers is Starburst® polymers (trademark of The Dow Chemical Company) where the dendrimer is a polyamidoamine (PAMAM).] A variety of suitable applications for such conjugates are broadly discussed in U.S. Pat. No. 5,338,532, including the use of these conjugates as delivery vehicles for biologically active agents. However, the U.S. Pat. No. 5,338,532 does not specifically teach, claim, or even mention the use of polymer conjugates as delivery vehicles for antineoplastic agents, e.g., cisplatin, carboplatin, titanocene dichloride and diorganotin dihalides or other anitneoplactic agents. U.S. Pat. 5,338,532 only exemplifies the use of zero valence metals, and ionic or radioactive metals, specifically exemplifying Fe, Rh, Pd, Y, Fn, Pb, Gd, Mn and Gd.

In the interval between the filing of this continuation-in-part and the filing of U.S. Ser. No. 09/111,232, a journal article on the matter originally claimed, written by two of the present inventors, was published [see "Detidrimer-platinate: a Novel Approach to Cancer Chemotherapy", *Anti-Cancer Drugs*, 10, 767–776 (1999)]. This article deals specifically with the formation of a dendrimer-cisplatin conjugate, i.e. a dendrimer-platinate. Although cisplatin is itself a platinum antineoplastic, the class as a whole is not taught by the article nor is it suggested that the methods of this article could be used or would be expected to work for the association of a dendrimer with other antineoplastic platinum-based analogues nor that the cisplatin is carried in the interior of the dendrimer.

SUMMARY OF THE INVENTION

This invention pertains to dendritic polymer conjugates which are useful drug delivery systems for carrying cisplatin, carboplatin, oxaliplatin, tetraplatin, platinum-DACH, ormaplatin, titanocene dichloride, vanadocene dichloride, niobocene dichloride, molybdenocene dichloride, rhenocene dichloride, diorganotin dihalides or other metallocene dihalides (hereinafter "antineoplastic dendritic polymer conjugates"); preferably cisplatin and carboplatin and other platin-based analogues (hereafter "platin-based analogue dendritic polymer conjugates"); more preferably cisplatin (hereafter "cisplatin dendritic polymer conjugates"), as antineoplastic agents to malignant tumors. The invention also pertains to methods of treating malignant tumors using these antineoplastic dendritic polymer conjugates, and to a method of preparing an antineoplastic dendritic polymer conjugate useful for carrying platinum (Pt), titanium (Ti), vanadium (V), niobium (Nb), molybdenum (Mo), rhenium (Re), or tin (Sn) containing agents (collectively "antineoplastic agents") to malignant tumors.

Antineoplastic dendritic polymer conjugates of this invention comprise a dendritic polymer conjugated to an antineoplastic agent, forming an antineoplastic dendritic polymer conjugate, e.g., especially a platin-based analogue dendritic polymer conjugate. These antineoplastic dendritic polymer conjugates are prepared by obtaining a dendritic polymer having functional or chelational groups which are accessible to a antineoplastic agent and capable of interacting with the functional or chelational groups, contacting the dendritic polymer with the antineoplastic agent, and thereby associating the dendritic polymer with this antineoplastic agent by means of covalent and/or non-covalent interactions (i.e. physically encapsulated or entrapped within the interior of the dendrimer, dispersed partially or fully throughout the dendrimer, or attached or linked to the dendrimer or any combination thereof, whereby the attachment or link-age is by means of covalent bonding, hydrogen bonding, adsorption, adsorption, metallic bonding, dipole-dipole interaction, van der Waals forces, or ionic bonding, or any combination thereof). These antineoplastic dendritic polymer conjugates are administered to in animal having a malignant tumor in an amount which is effective to inhibit growth of the malignant tumor, preferably intravenously (I.V.), although other methods such as oral, parental (I.P.), subcutaneous (S.C.), intramuscular, intraarterial, or topical administration are also possible.

The added matter in this continuation-in-part application involves the conjugation of the dendritic polymer via encapsulation internal within the dendrimer with an antineoplastic agent as well as the chelation of the antineoplastic agent to the interior or exterior of the dendrimer.

The antineoplastic dendritic polymer conjugate results in an anti-tumor agent that exhibits unexpected and surprisingly high efficacy, drug carrying capacity, and dosage capabilities. The antineoplastic dendritic polymer conjugate also shows a surprising and unexpected decrease in toxicity, good water solubility, good stability on storage, and improved anti-tumor activity in vivo. Most significantly, these antineoplastic dendritic polymer conjugates were found to be active against B16F10 tumor models, which are known to be resistant to cisplatin at its maximum tolerated dose via I.V. administration (about 1 mg/kg).

BRIEF DESCRIPTION OF THE DRAWINGS

FIGS. 10A and 10B are each a structural representation of possible variations in platinum binding to dendrimer;

FIG. 11 is a graph showing the release of cisplatin from a dendrimer-platinate at two physiological pH conditions at 72 hours and 37° C.;

DESCRIPTION OF THE PREFERRED EMBODIMENTS

Figure 1:
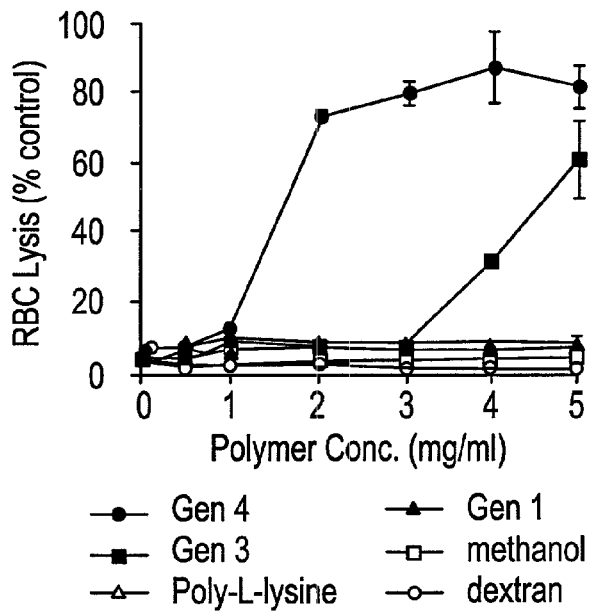
FIG. 1 is a graph showing the effect of cationic dendrimers on hemolysis of rat erythrocytes at 1 hour.

The dendritic polymers which may be used to form antineoplastic dendritic polymer conjugates include generally any of the known dendritic architectures including dendrimers, controlled hyperbranched polymers, dendrigrafts, and random hyperbranched polymers. Dendritic polymers are polymers with densely branched structures having a large number of reactive groups A dendritic polymer includes several layers or generations of repeating units which all contain one or more branch points. Dendritic polymers, including dendrimers and hyperbranched polymers, are prepared by condensation reactions of monomeric units having at least two reactive groups after attachment. The dendrimers that can be used include those comprised of a plurality of dendrons that emanate from a common core which can be a single atom or a group of atoms. Each dendron generally consists of terminal surface groups, interior branch junctures having branching functionalities greater than or equal to two, and divalent connectors that covalently connect neighboring branching junctures. For a review article of this area see, for example, Donald A. Tomalia, et al., *Angew. Chem. Int. Engl.* 29, 138–175 (1990).

Dendrons and dendrimers can be prepared by convergent or divergent synthesis.

Divergent synthesis of dendrons and dendrimers involves a molecular growth process which occurs through a consecutive series of geometrically progressive step-wise additions of branches upon branches in a radially outward molecular direction to produce an ordered arrangement of layered branched cells. Each dendritic macromolecule includes a core branch cell, one or more layers of internal branch cells, and an outer layer of surface branch cells, wherein each of the cells includes a single branch juncture. The cells can be the same or different in chemical structure and branching functionality. The surface branch cells may contain either chemically reactive or passive functional groups. Chemically reactive surface groups can be used for further extension of dendritic growth or for modification of dendritic molecular surfaces. The chemically passive groups may be used to physically modify dendritic interiors or dendritic surfaces, such as to adjust the ratio of hydrophobic to hydrophilic terminals. In this fashion one can improve the solubility of a guest molecule in the interior of the dendritic polymer or the solubilization of the dendritic container in a particular solvent. (See for example for dense star polymers U.S. Pat. Nos. 4,507,466; 4,588,120; 4,568,737; 4,631,337; 4,587,329; and 4,737,550; WO 84/02705; EP 0115771; and EP 0608908; for rod shaped dense star polymers U.S. Pat. No. 4,694,064; EP 02344008; and EP 0556871; for hydrophobic outer shell dense star polymers U.S. Pat. No. 5,560,929; and EP 0680495, all the disclosures of which are hereby incorporated by reference.)

Convergent synthesis of dendrimers and dendrons involves a growth process, which begins from what will become the surface of the dendron or dendrimer, and progresses radially in a molecular direction toward a focal point or core. (See for example U.S. Pat. No. 5,041,516, the disclosure of which is hereby incorporated by reference.) The dendritic polymers may be ideal or non-ideal, i.e., imperfect or defective. Imperfections are normally a consequence of either incomplete chemical reactions, or unavoidable competing side reactions. In practice, real dendritic polymers are generally nonideal, i. e., contain certain amounts of structural imperfections.

The hyperbranched polymers which may be used represent a class of dendritic polymers which contain high levels of nonideal, irregular branching as compared with the more nearly perfect regular structure of dendrons and dendrimers. Specifically, hyperbranched polymers contain a relatively high number of irregular branching areas in which not every repeat unit contains a branch juncture. The preparation and characterization of dendrimers, dendrons, random hyperbranched polymers, controlled hyperbranched polymers, and dendrigrafts (collectively "dendritic polymer") is well known. Examples of dendrimers and dendrons, and methods of synthesizing the same are set forth in U.S. Pat. Nos. 4,410,688, 4,507,466; 4,558,120; 4,568,737; 4,587,329; 4,631,337; 4,694,064; 4,713,975; 4,737,550; 4,871,779 and 4,857,599, the disclosures of which are hereby incorporated by reference. Examples of hyperbranched polymers and methods of preparing the same are set forth, for example in U.S. Pat. Nos. 5,418,301 and 5,514,764, the disclosures of which are hereby incorporated by reference. Examples of dendrigrafts and methods of preparing the same are set forth, for example in an article by D. A. Tomalia and R. Esfand, *Chem. & Ind.,* 416–420 (Jun. 2, 1997).

The dendritic polymers or macromolecules useful in the practice of this invention are characterized by a relatively high degree of branching, which is defined as the number average fraction of branching groups per molecule, i.e., the ratio of terminal groups plus branch groups to the total number of terminal groups, branched groups and liner groups. For ideal dendrons and dendrimers, the degree of branching is 1; whereas for linear polymers, the degree of branching is 0 and hyperbranched polymers have a degree of branching that is intermediate to that of linear polymers and ideal dendrimers, preferably of at least about 0.5 or higher. The degree of branching is expressed as follows:

$$f_{br} = \frac{N_t + N_b}{N_t + N_b + N_l}$$

where $N_x$ is the number of type x units in the structure. Both terminal (type t) and branched (type b) units contribute to the fully branched structure whilst linear (type 1) units reduce the branching factor; hence $$0 \leq f_{br} \leq 1$$

where $f_{br}=0$ represents the case of a linear polymer and $f_{br}=1$ represents the case of a fully branched macromolecule.

Dendritic polymers suitable for use with the present invention also include macromolecules commonly referred to as cascade molecules [e.g., E. Buhleier et al., *Synthesis* 155–158 (February 1978)], arborols [e.g., U.S. Pat. Nos. 5,376,690 and 5,210,309], arborescent grafted molecules, tectodendrimers [e.g., Srinivas Uppuluri et al., "Tecto(dendrimer) Core-shell Molecules: Macromolecular Tectonics for the Systematic Synthesis of Larger Controlled Structure Molecules" PMSE, Spring Meeting (Mar. 21–25, 1999) 55–56], and the like. Suitable dendritic polymers also include bridged dendritic polymers, i.e., dendritic macromolecules linked together either through surface functional groups or through a linking molecule connecting surface functional groups together, and dendritic polymer aggregates held together by physical forces. Also included are spherical-shaped dendritic polymers (e.g., U.S. Pat. Nos. 4,507,466; 4,588,120; 4,568,737; 4,631,337; 4,587,329; and 4,737,550, the disclosures of which are hereby incorporated by reference) and rod-shaped dendritic polymers (e.g., U.S. Pat. No. 4,694,064, the disclosure of which is hereby incorporated by reference) grown from a polymeric core. Additional dendritic polymers suitable for use with the present invention include all the basic dendritic structures where specific chelating groups or moieties are either in the central core of the dendrimer, and/or located within the interior structure on the dendron arms and/or located on the surface of the dendrimer. All of these above dendrimer terms are to be understood to be included within the term "dendritic polymer."

The dendritic polymers used in the practice of this invention can be generationally monodisperse or generationally polydisperse. Dendritic polymers in a monodisperse solution are substantially all of the same generation, and hence of uniform size and shape. The dendritic polymers in a polydisperse solution comprise a distribution of different generation polymers. The dendritic polymer molecules which may be used in the practice of this invention include mixtures of different interior and exterior compositions or functionalities. Examples of suitable dendritic polymers include poly(ether) dendrons, dendrimers and hyperbranched polymers, poly(ester) dendrons, dendrimers and hyperbranched polymers, poly(thioether) dendrons, dendrimers and hylperbranched polymers, poly(amino acid) dendrons, dendrimers and hyperbranched polymers, poly(arylalkylene ether) dendritic polymers and poly(propyleneimine) dendrons, dendrimers and hyperbranched polymers. Poly(amidoamine) (PAMAM) dendrimers have been found to be particularly useful for preparing the metal-containing antineoplastic dendritic polymer conjugates of this invention.

Dendritic polymers which are useful in the practice of this invention include those that have symmetrical branch cells (arms of equal length, e.g., PAMAM dendrimers; for example described in U.S. Pat. No. 5,527,524) and those having unsymmetrical branch cells (arms of unequal length, e.g. lysine-branched dendrimers, for example described in U.S. Pat. No. 4,410,688), branched dendrimers, cascade molecules [e.g., E. Buhleier et al., *Synthesis* 155–158 (February 1978)], arborols [e.g., U.S. Pat. Nos. 5,376,690 and 5,210,309], and the like.

The term "dendritic polymer" also includes so-called "hyper comb-branched" polymers. These comprise non-crosslinked poly-branched polymers prepared by (1) forming a first set of linear polymer branches by initiating the polymerization of a first set of monomers which are either protected against or non-reactive to branching and grafting, during polymerization, each of the branches having a reactive end unit upon completion of polymerization, the reactive end units being incapable of reacting with each other; (2) grafting the branches to a core molecule or core polymer having a plurality of reactive sites capable of reacting, with the reactive end groups on the branches; (3) either deprotecting or activating a plurality of monomeric units on each of the branches to create reactive sites; (4) separately forming a second set of linear polymer branches by repeating step (1) with a second set of monomers; (5) attaching the second set of branches to the first set of branches by reacting the reactive end groups of the second set of branches with the reactive sites on the first set of branches, and then repeating steps (3), (4) and (5) above to add one or more subsequent sets of branches. (Such hyper comb-branched polymers are disclosed in European Patent Publication 0473088A2 which are generally referred to as "dendrigraft polymers", the disclosure of which is hereby incorporated by reference.) A representative formula for such hyper comb-branched polymer is:

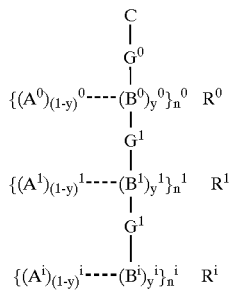

wherein C is a core molecule; each R is the residual moiety of an initiator selected from a group consisting of free radical initiators, cationic initiators, anionic initiators, coordination polymerization initiators and group transfer initiators; A and B are polymerizable monomers or comonomers capable of withstanding the conditions required for branching therefrom or grafting thereto, at least during the polymerization of the $\{(A)\text{-}(B)\}$ linear polymer chain and during its grafting to a prior $\{(A)\text{-}(B)\}$ branch of the $\{(A)\text{-}(B)\}$ core branch; each G is a grafting component and the designation

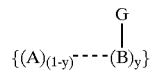

indicates that G can attach to either an (A) unit or a (B) unit; n is the degree of polymerization of the indicated generation comb-branches; y is the fraction of B units in the indicated generation branch, and has a value of 0.01 to 1; the superscripts 0, 1 and i designate the comb-branch generation level, with i beginning at "2" and continuing for the number of reiterative branch set generations in the polymer; and at least $n^0$ and n' are $\geqq 2$.

For purposes of clarifying terminology, it should be noted that dense star dendrimers are built by reiterative terminal branching, while hyper comb-branched dendrimers are built by reiterative comb-branching. In dense star dendrimers, subsequent generation branches are attached to the terminal moieties of a previous generation, thus limiting the degree of branching to the functionality of the previous generation terminal moiety, which would typically be two or three. In contrast, by branching oligomers upon prior generation oligomer branches in accordance with hyper comb-branched dendrimer, one can dramatically increase the degree of branching from generation to generation, and indeed can vary the degree of branching from generation to generation.

The dendritic polymers which are believed to be most useful in the practice of this invention are approximately monodispersed. That is, dendritic polymers in a monodispersed solution in which all of the dendritic polymer molecules are substantially of the same generation, and hence of uniform size and shape, are preferred. Monodispersed solutions of dendrimers are particularly preferred.

The dendritic polymers used in the practice of this invention have internal and/or terminal functional or chelational groups which are accessible to an antineoplastic agent which is capable of associating with the functional or chelational groups, thereby allowing for the uptake of the antineoplastic agent by the dendritic polymer. Dendritic polymers having anionic terminal functional groups are preferred. Examples of anionic terminal function groups include sulfonates, sulfates and carboxylate groups, with carboxylate or carboxylic groups, including the sodium and potassium salts thereof, being particularly preferred. While not wishing to be bound by theory, it is believed that the advantageous results of the present invention are obtained because the platin form of the Pt permits it to be active, usually in its hydrated form, in the interior of the dendrimer, and at the cancer cell site it is unloaded or released from the dendrimer in its active form, still believed to be the hydrated form, and then the Pt is able to cross-link with the DNA of the cancer cell and thereby inhibit the proliferation of the cancer cells. When the EPR antineoplastic dendritic polymer conjugate is injected upstream of the tumor mass it will enter easily as it size is controlled by the dendrimer and the tumor has a large incoming blood flow and it will not leak to the surrounding area as the vascular size leaving the tumor is more restricted and the dendrimer size too large for those vessels. Thus a high concentration of the drug is kept in the tumor. [See for example UM. Ohndorf et al., *Nature* 399, 708–712 (Jun. 17, 1999).] While not wishing to be bound by theory, it is believed that the advantageous results of the present invention are obtained because the antineoplastic agents are positively charged and are attracted to the negative charge of the carboxylic groups on the dendrimer and with a higher osmotic pressure on the outside of the dendrimer than its interior a shunting of the antineoplastic agent occurs to move it into the interior of the dendrimer.

Encapsulation or entrapment is a chemical or physical interaction based on ionic or any other form of association between two compounds (e.g., covalent bonding, hydrogen bonding, adsorption, absorption, metallic bonding, van der Waals forces between a host molecule (dendritic polymer) and a guest molecule (an antineoplastic agent). Encapsulation can be reversible or irreversible. The dendrimer and antineoplastic agent encapsulation of the present invention defines the dendrimer to act as a host, port, or site for the antineoplastic agent, i.e., cisplatin or carboplatin. In the area of polymer chemistry because dendrimers have specific structural related properties, encapsulation is a more defined and accurate term. In contrast, with linear polymers where it is not really clear where the drug is bound or associated to the polymer, the term entrapment is more commonly used.

It is also possible to covalently attach an antineoplastic agent to the dendrimer. This covalent attachment may be directly between the surface of the dendrimer and the antineoplastic agent or by means of a linker moiety between the surface of the dendrimer and the antineoplastic agent. Some linkers that may be used are described in U.S. Pat. No. 5,527,524; EP 0353450; EP 0570575; and EP 0296522, the disclosures of which are hereby incorporated by reference.

Examples of suitable dendritic polymers which may be used in the practice of this invention include poly(amidoamine) dendrimers, especially carboxylate terminated poly(amidoamine) dendrimers, and carboxylate terminated poly(propyleneimine) dendrimers, especially where these carboxylic acid groups have formed salts, especially sodium or potassium.

The generation of the dendritic polymer, and hence the size of the dendritic polymer, which may be utilized in the practice of this invention may vary considerably. For example, generation 3.5 poly(amidoamine) dendrimers (3.5 PAMAM) are acceptable for use in the practice of this invention. However, higher and lower generations are also expected to be useful, but especially the range from generation 3.5 to 7.5 for PAMAM dendrimers having an ethylenediamine (EDA) core.

The antineoplastic agent can be generally any antineoplastic agent, especially a platin-based analogue, which can be reversibly conjugated to or associated with the dendritic polymer and which exhibits anti-tumor activity when released from the dendritic polymer. An antineoplastic agent is a therapeutic compound used for the treatment of neoplastic diseases, such as ovarian cancer, lung cancer, testicular cancer, breast cancer, stomach cancer and lymphoma. An antineoplastic agent, as used herein, is as defined before. Examples of such antineoplastic agents include, but are not limited to, cisplatin, carboplatin, oxaliplatin, tetraplatin, platinum-DACH, ormaplatin, titanocene dichloride, vanadocene dichloride, niobocene dichloride, molybdenocene dichloride, rhenocene dichloride, diorganotin dihalides or other metallocene dihalides. The preferred antineoplastic agent is a platinum containing compound, e.g., a platin-based analogue. More preferred are cisplatin (cis-diamminedichloroplatinum) [see B. Rosenberg et al., *Nature* 205, 698 (1965), German Patents 2,318,020 and 2,329,485] and carboplatin (cis-diammine(1,1-cyclobutanedicarboxylato) platinum) [see U.S. Pat. No. 4,140,707]. Other suitable platinum containing compounds include those having a tetravalent platinum atom bonded to the nitrogen of two amine ligands, which may be the same or different, the amine ligands being in cis conformation with respect to each other, the remaining ligands may be capable of interacting with or being displaced by a functional group of the dendritic polymer. An example of such a compound is cis-diamminedichloroplatinum. A large number of different analogues of cisplatin have been investigated [see for example; J. Respondek and J. Engel, *Drugs Of The Future,* 21(4), 391–408 (1996) and R. B. Weiss and M. C. Christian, *Drugs,* 46, 360–377 (1993)] and many of these different platinum-derivatives are likely to be useful in the present invention and are included within the term "platin-based analogues".

The antineoplastic dendritic polymer conjugates may be prepared by dissolving the dendritic polymer in a suitable solvent, such as water, contacting the dissolved dendritic polymer with a dissolved antineoplastic agent under conditions sufficient to cause the antineoplastic agent to associate with the dendritic polymer and to form a dendritic polymer antineoplastic conjugate. A cisplatin to dendrimer (Generation 3.5 PAMAM, EDA core, dendrimer) molar ratio of 35:1 was used in the experiments described in the examples and these conditions resulted in a compound that was composed of aggregated dendrimers found to be 44 nm in diameter as that aggregate by GPC and PCS. The ratio of cisplatin molecules to dendritic polymer molecules can vary considerably. Cisplatin dendritic polymer conjugates having a cisplatin to dendritic polymer molar ratio of from about 100:1 to about 1:1 have been evaluated and are expected to provide practical advantages. The large size of this compound in comparison to the dendrimer itself (4 nm) could be caused by the formation of intermolecular bonds between dendrimers which are mediated by cisplatin. It is possible that by changing the ratio of cispiatin, or other platin-based analogues, to dendrimer that it would be possible to produce materials which have different average sizes and also potentially different biological properties. Preferably, the antineoplastic agents of the present invention would be encapsulated within the dendrimer. This is likely to occur via an ionic shunt mechanism, whereby the anionic groups (e.g., carboxylate groups) of the surface of the dendritic polymer are responsible for a weak dendrimer-antineoplastic agent interaction that allows for the antineoplastic agent to be uptaken by the dendrimer (i.e., primary interaction), possibly proceeding through a reaction between the interior nitrogen groups of the dendrimer and the antineoplastic agent (i.e., secondary interaction). This ionic shunt mechanism results in the encapsulation of the antineoplastic agent within the dendritic polymer.

The antineoplastic dendritic polymer conjugates may be administered to animals, especially humans, in a therapeutically effective amount to treat a malignant tumor in the animal. The antineoplastic dendritic polymer conjugates may be administered orally or topically, but are preferably administered parentally, such as by subcutaneous (S.C.) injection, intraperitoneal (I.P.) injection, intravenous (I.V.) injection, intraarterial injection or intramuscular injection. An effective amount of a generation 3.5 poly(amidoamine) dendrimer-cisplatin conjugate in which the cisplatin loading is about 25% by weight (i.e., 25% by weight of the conjugate is cisplatin) has been found to be from about 1 milligram per kilogram of body weight to about 15 milligrams per kilogram of body weight for a mouse (DBA2 or C57) for an intraperitoneal injection. Suitable quantities of various antineoplastic dendritic polymer conjugates which are therapeutically effective in the treatment of various malignant tumors in other animals can be determined through routine experimentation and testing.

It is anticipated that the antineoplastic dendritic polymer conjugates will be effective in the treatment of various malignancies in which cisplatin, carboplatin and other antineoplastic agents as anti-tumor agents have been found to be therapeutically affective, including ovarian cancer, lung cancer, testicular cancer, breast cancer, stomach cancer and lymphoma. Also it is anticipated that the antineoplastic dendritic polymer conjugates could be used in combination therapy with other anticancer agents (i.e., synergistic application). In vitro testing and in vivo testing on mice suggest that the antineoplastic dendritic polymer conjugates, especially the platin-based analogues, are also therapeutically effective in the treatment of melanoma and human lymphoblastic leukemia.

Glossary of Terms in the Examples:
AAS means atomic absorption spectroscopy
AUC means area under the curve
BDH means BDH Laboratory Supplies in Dorest, England
cisplatin means cis-diamminedichloro platinate (II)
carboplatin means cis-diammine(1,1-cyclobutanedicarboxylato)platinate (II)
DDW means double deionized water
DMSO means dimethylsulfoxide
EDA means ethylenediamine
EPR means enhanced permeability retention
FCS means fetal calf serum
GPC means gel permeation chromatography
I.P. means intraperitoneal
IR means infrared spectroscopy
I.V. means intravenous
MEM means minimal essential media
MTT means 3-(4,5-dimethyltiazol-2-yl)-2,5-diphenyl tetrazolium bromide (a colorimetric dye which is a pale yellow substrate that is cleaved by living cells to yield a dark blue formazan product)
MWCO means molecular weight cut off
NMR means nuclear magnetic resonance spectroscopy
OD means optical density
OPDA means o-phenylenediamine assay (added to perform photometry assay for metals)
PAMAM means poly(amidoamine) dendrimers
PBS means phosphate buffered saline
POPAMS means poly(propyleneimine) dendrimers
PSC means particle sizing by photon correlation spectroscopy
RPMI media means Roswell Park Memorial Institute media, usually RPMI—1640, see G. E. Moore and L. K. Woods, "Culture Media for Human Cells—RPMI 1603,, RPMI 1634, RPMI 1640 and RPMI GEM 1717", Tissue Culture Assoc. Manual 3, 503–508 (1976)
S.C. means subcutaneous Experimental Methods Synthesis and Characterization Poly(amidoamine) dendrimers (PAMAM, EDA core) (Sigma) were synthesized according to the method of Tomalia et al., Polymer J., 17, 117–132(4) (1985). Dendrimers of generation 3.5 (COONa) and 4 ($NH_2$) were allowed to interact with cisplatin under stirring conditions at room temperature for 4 hours during which time chloride ion release was followed using a chloride electrode.

| Dendrimer Generation | MW (Daltons) | No. Funct. Groups |
| --- | --- | --- |
| 4.0 | 14,215 | 64 ($NH_2$) |
| 3.5 | 12,419 | 64 (COONa) |

The dendrimer-platinum (Pt) was characterized using the OPDA (colorimetric) assay and AAS (total Pt), GPC (Mw and free Pt), IR and NMR.

Pt Release

To study the rate of Pt release and also dendrimer biodegradation the conjugate was incubated in buffers at pH 7.4 and 5.5 and also in the presence of serum and lysosomal enzymes.

Biological Evaluation

In vitro cytotoxicity was assessed against B16F10 melanoma, CCRF (human lymphoblastic leukemia) and Cor-L23 (human lung) cells using the MTT assay. Dendrimer-Pt and free cisplatin were administered I.P. (days 1,2,3 or day 1 only) to DBA2 or C57 mice bearing I.P. inoculated L1210 or B16F10 tumors (respectively). Alternatively drug was administered I.V. to mice bearing S.C. implanted B16F10 when the tumor reached palpable size (50–100 $mm^2$). Animal weight, tumor size and animal survival were monitored (UK guidelines for animal experiments involving neoplasia were followed.)

Materials

Polyamidoamine (PAMAM, EDA core) Starburst® dendrimers (trademark of The Dow Chemical Company) were purchased from Aldrich (UK) Ltd.

The following examples further illustrate the invention but are not considered as a limitation on the scope of the invention.

EXAMPLES

Example 1

Figure 2:
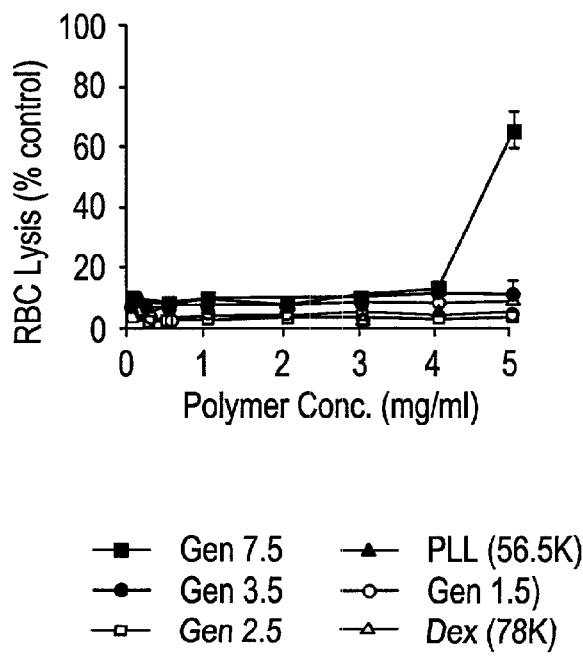
FIG. 2 is a graph showing the effect of anionic dendrimers on hemolysis of rat erythrocytes at 1 hour.

Effect of PAMAM Dendrimer on the Stability of Rat Erythrocytes Incubated in vitro Method Poly(amidoamine) dendrimers (cationic and anionic) of increasing generations were incubated with rat erythrocytes obtained from an adult Wistar rat. The interaction of the dendrimer with the erythrocyte was assessed spectrophotometrically by the detection of released hemoglobin, induced by lysis, with a. spectrophotometer at 550 nm. Various concentrations of dendrimer, controls (methanol (BDH)), poly-L-lysine (HBr salt—56.5 KD Mw (Sigma)), and dextran (74 KD Mw (Sigma)) (dissolved in physiologically buffered saline) were incubated with the rat erythrocytes (2% w/v solution) for 1 hour at 37° C., and at 10 rpm (shaking water bath). On completion, the erythrocytes were spun in a centrifuge at 1500× g for 10 minutes to pellet the cells and 100 μl of the supernatant was removed and analyzed on the spectrophotometer after blanking against PBS. The results are expressed in FIGS. 1 and 2 as a percentage of hemoglobin release compared to an intrinsic control (Tritonx100 (1% v/v solution (Sigma)) which gave 100% lysis.

Result

Cationic dendrimers, except generation 1, were lytic, whereas soluble anionic dendrimers (including PAMAM generation 3.5) were not lytic.

Example 2

Cell Cytotoxicity of Unmodified Dendrimers Against B16F10 cells

Method

B16F10 cells are an adherent murine melanoma cell line. B16F10 cells were seeded at a density of $1\times10^5$ cells per ml ($1\times10^4$ cells per well) in a 96 well flat bottomed microtitre plate (Costar) in RPMI 1640 tissue culture media (Gibco) supplemented with 10% FCS (Gibco). All cellular growth and cytotoxic incubations were carried out in a cell incubator at 37° C. and 5% $CO_2$ atmosphere.

Cell density was assessed using an improved neurenbrow hemocytometer (Sigma). The cells were washed with PBS twice and fresh RPMI media (supplemented with FCS) was added, and the cells were then seeded in a microtitre plate. The cells were left for 24 hours to recover and re-adhere.

Figure 3:
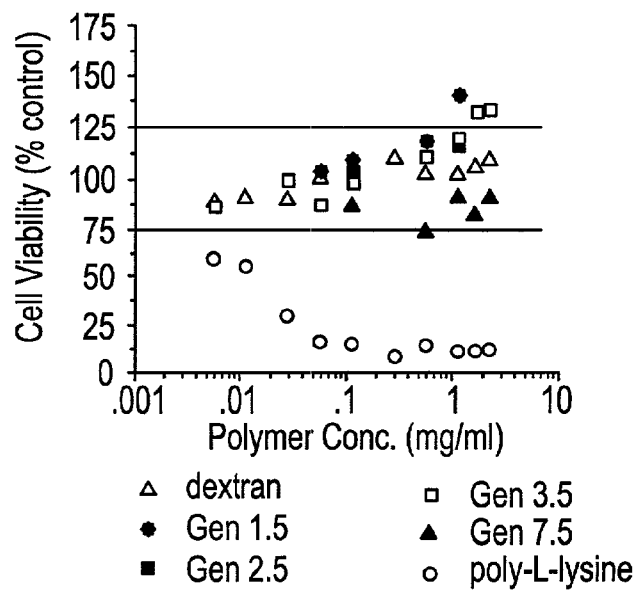
FIG. 3 is a graph showing the effect of anionic dendrimers on B16F10 cells at 72 hours.
Figure 4:
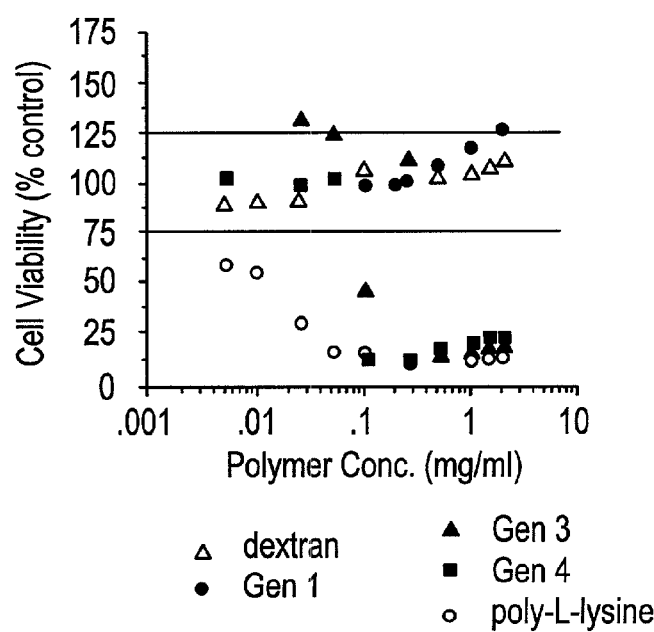
FIG. 4 is a graph showing the effect of cationic dendrimers on B16F10 cells at 72 hours.

All polymers and controls were dissolved in RPMI media (supplemented with FCS) and then sterilized through a 0.2 $\mu$m sterile filter (Acrodisk), the first few microliters of the solution being discarded in the case of adherence of the polymer to the filter membrane. Polymer and controls were then added in increasing concentrations to the cells in the microtitre plate. Some cells were left in media only to act as cellular controls. The methanol and poly-L-lysine were negative controls and the dextran was a positive control. The cells were left in the incubator for 72 hours, and checked occasionally for yeast or bacterial contamination. Five hours prior to the incubation time end point, at 67 hours, 20 $\mu$l of MTT was added and the cells left for the final 5 hours. Then cellular media was removed, 100 $\mu$l of optical grade DMSO (Sigma) was added and the MTT crystals dissolved. The plates were read in a Titerteck plate reader and the results (OD) are expressed in FIGS. 3 and 4 as a percentage of the OD seen in cell wells containing no polymer or control.

Result

Cationic dendrimers were cytotoxic (similar to poly-L-lysine) towards the cell line, while anionic dendrimers (including PAMAM generation 3.5, EDA core) were not cytotoxic (similar to dextran).

Example 3

Cell Cytotoxicity of Unmodified Dendrimers Against CCRF-CEM Cells

Method

CCRF-CEM cells are lymphoblastic leukemia and a suspension cell line, i.e. it grows in suspension. CCRF-CEM cells were seeded at a density of $5\times10^4$ cells per ml ($5\times10^3$ cells per well) in a 96 well V-shape microtitre plate (Costar) in RPMI 1640 tissue culture media (Gibco) supplemented with 10% FCS (Gibco). All cellular growth and cytotoxic incubations were carried out in a cell incubator at 37° C. and 5% $CO_2$ atmosphere.

Cell density was assessed using an improved neurenbrow hemocytometer (Sigma). The cells were centrifuged at 1000×g and resuspended in fresh media (supplemented with FCS) before the cell density was assessed. The cells were then seeded in a microtitre plate. The cells were left for 24 hours to recover and re-adhere.

Figure 5:
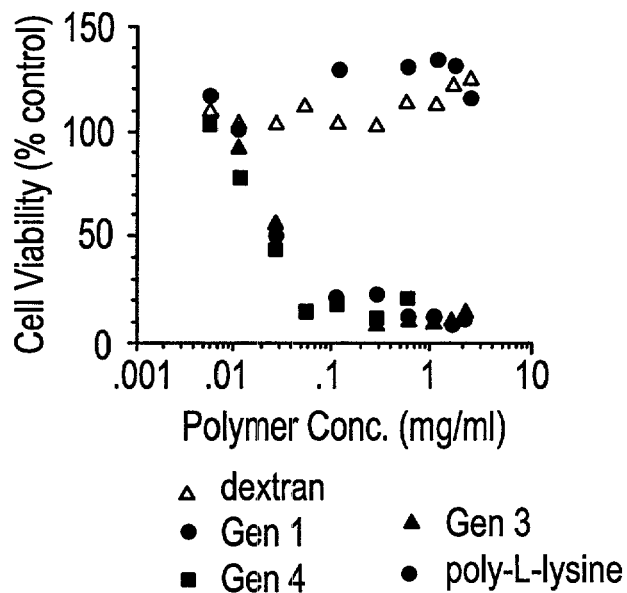
FIG. 5 is a graph showing the effect of cationic dendrimers on CCRF-CEM cells at 72 hours.
Figure 6:
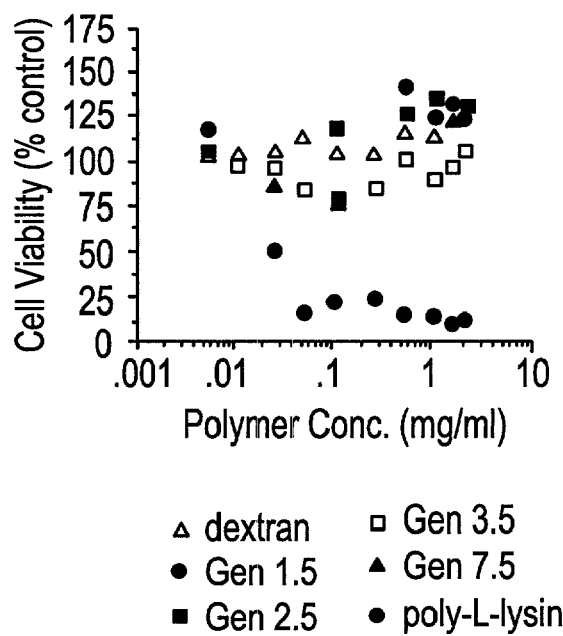
FIG. 6 is a graph showing the effect of anionic dendrimers on CCRF-CEM cells; at 72 hours

All polymers and controls were dissolved in RPMI media (supplemented with FCS) and then sterilized through a 0.2 $\mu$m sterile filter (Acrodisk), the first few microliters of the solution being discarded in the case of adherence of the polymer to the filter membrane. Polymer and controls were then added in increasing concentrations to the cells in the microtitre plate. Some cells were left in media only to act as cellular controls. The methanol and poly-L-lysine were negative controls and the dextran was a positive control. The cells were left in the incubator for 72 hours, and checked occasionally for yeast or bacterial contamination. Five hours prior to the incubation time end point, at 67 hours, 20 $\mu$l MTT was added, and the cells left for the final 5 hours. Then cellular media was removed, 100 $\mu$l of optical grade DMSO (Sigma) was added and the MTT crystals dissolved. The plates were read in a Titerteck plate reader and the results (OD) are expressed in FIGS. 5 and 6 as a percentage of the OD seen in cell wells containing no polymer or control.

Result

Cationic dendrimers were cytotoxic (similar to poly-L-lysine) towards the cell line, while anionic dendrimers (including PAMAM generation 3.5) were not cytotoxic (similar to dextran).

Example 4

Cell Cytotoxicity of Unmodified Dendrimers Against HepG2 Cells

Method

HepG2 is a hepatocellular carcinoma and is an adherent cell line, i.e. it grows in a monolayer. HepG2 cells were seeded at a density of $1\times10^5$ cells per ml ($1\times10^4$ cells per well) in a 96 well flat bottomed microtitre plate (Costar) in MEM tissue culture media (Gibco) supplemented with 10% FCS (Gibco). All cellular growth and cytotoxic incubations were carried out in a cell incubator at 37° C. and 5% $CO_2$ atmosphere.

Cell density was assessed using an improved neurenbrow hemocytometer (Sigma). The cells were washed with PBS twice and fresh RPMI media (supplemented with FCS) added, the cells were then seeded in a microtitre plate. The cells were left for 24 hours to recover and re-adhere.

Figure 7:
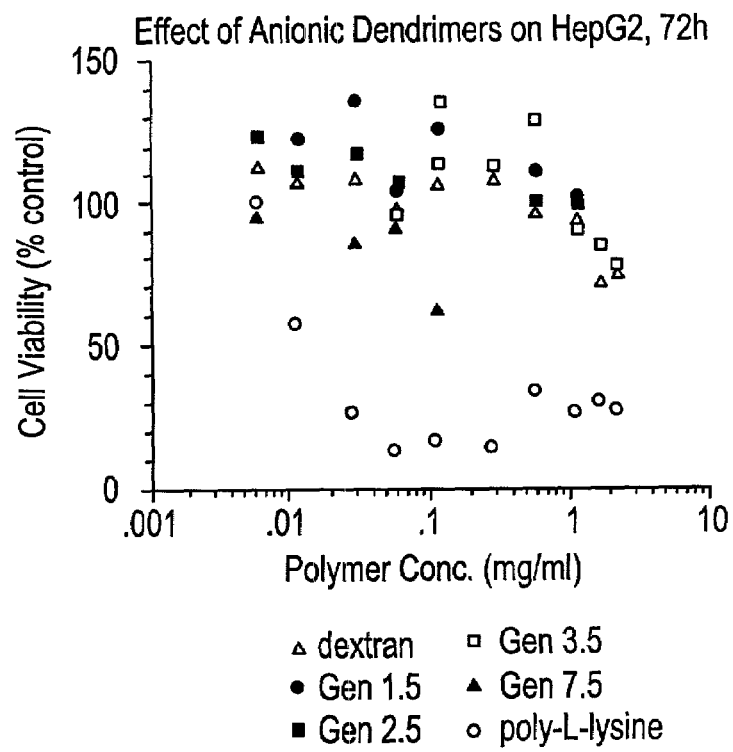
FIG. 7 is a graph showing the effect of anionic dendrimers on HepG2 cells at 72 hours.
Figure 8:
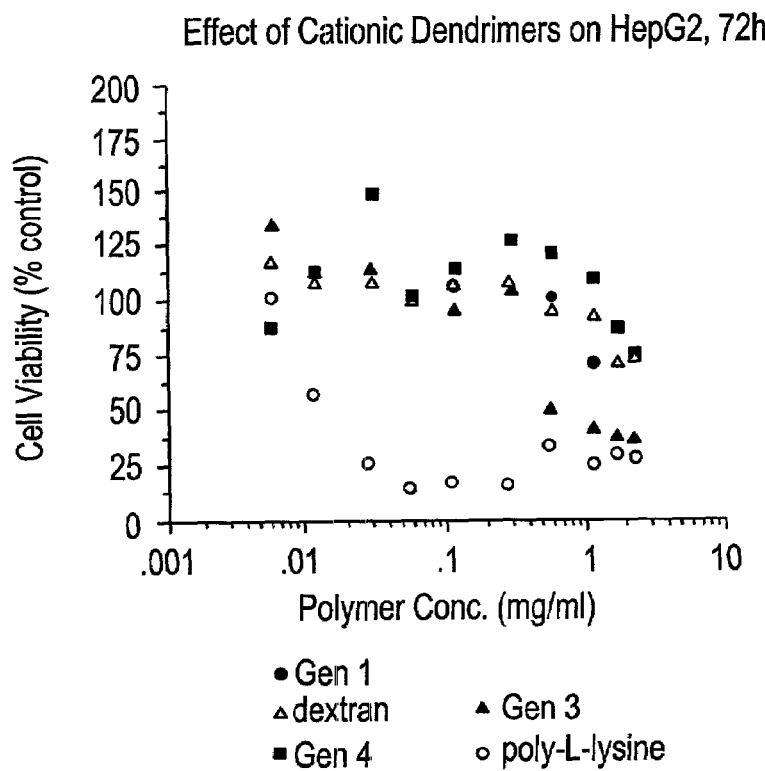
FIG. 8 is a graph showing the effect of cationic dendrimers on HepG2 cells at 72 hours.

All polymers and controls were dissolved in RPMI media (supplemented with FCS) and then sterilized through a 0.2 $\mu$m sterile filter (Acrodisk), the first few microliters of the solution being discarded in the case of adherence of the polymer to the filter membrane. Polymer and controls were then added in increasing concentrations to the cells in the microtitre plate. Some cells were left in media only to act as cellular controls. The methanol and poly-L-lysine were negative controls and the dextran was a positive control. The cells were left in the incubator for 72 hours, and checked occasionally for yeast or bacterial contamination. Five hours prior to the incubation time end point, at 67 hours, 20 $\mu$l of MTT was added and the cells left for the final 5 hours. The cellular media was removed and 100 $\mu$l of optical grade DMSO (Sigma) was added and the MTT crystals dissolved. The plates were read in a Titerteck plate reader and the results (OD) are expressed in FIGS. 7 and 8 as a percentage of the OD seen in cell wells containing no polymer or control.

Result

Cationic dendrimers were cytotoxic (similar to poly-L-lysine, MW 56 KDa) towards the cell line, while anionic dendrimers (including PAMAM gen. 3.5) were not cytotoxic (similar to dextran, MW 78 KDa).

Example 5A

Synthesis of a Cisplatin Dendritic Polymer Conjugate

Method 1 g of poly(amidoamine) Starburst® dendrimer, generation 3.5, EDA core, was dissolved in DDW—(10 ml). 0.8 g of cisplatin was dissolved in 400 ml of water (cisplatin maximum solubility is 2 mg/ml) (a molar ratio of cisplatin to dendrimer of 35:1). Once the cisplatin was fully dissolved in the water, the dendrimer was added dropwise under stirring to the cisplatin. The solution was left to react for at least 4 hours. Then the solution was transferred to a dialysis bag (10 KD MW cut off) and dialyzed against DDW for 2–3 days. The water was changed every few hours. The dendrimer-platinate was transferred to a glass container and freezed quickly using liquid nitrogen before being lyophilized (VA Howe). The above procedure was repeated but with varying molar ratios from 1–100 in incremental steps of 10 and the optimal ratio determined for the reaction.

Results

The weight percent was reproducibly determined at 25 wt %, while the maximum wt % achievable was approximately 40 wt %. The ratio experiment allowed estimation of the type of cisplatin binding.

Example 5B

Synthesis of a Carboplatin Dendritic Polymer Conjugate

Method 0.6964 g ($5.39 \times 10^{-5}$ mol) of poly(amidoamine) Starburst® dendrimer, generation 3.5, EDA core, was dissolved in 20 ml of 18Ω water (Bamstead-Nanopure). 0.666 g ($1.79 \times 10^{-3}$ mol) of carboplatin was dissolved in 300 ml 18Ω water (Barnstead-Nanopure) (a molar ratio of carboplatin to dendrimer of 33:1). This mixture was gently heated (35° C.) until the carboplatin was completely in solution. Once the carboplatin was fully dissolved in the water, the dendrimer was added dropwise, under nitrogen, and stirred over a period of 45 minutes. The solution was isolated from light and stirred under nitrogen at room temperature for 24 hours. The unreacted or excess carboplatin was removed using Centricon Plus-80 MWCO 5000 (Milhpore, Bioseparations). Upon recovery of the retentate, the isolated solution was lyophilized for 48 hours (The Labconco FreeZone 4.5 Lit.) to give the hygroscopic dendrimer-platinate as a fine white powder.

Results

The weight percent was determined to be at 20.47 wt % Pt.

Example 6

Generational Affect

Method

Poly(amidoamine) Starburst® dendrimers, EDA core, of generation 3.5, 4.5, and 5.5 with sodium carboxylic surface groups were each dissolved in 20 ml of 18Ω water (Bamstead-Nanopure) and then were reacted with cisplatin. A molar ratio of cisplatin to dendrimer of 33:1, 74:1, 127:1, respectively was used. The cisplatin was dissolved in 300 ml of 18Ω water (Barnstead-Nanopure) and gently heated (35° C.) until the cisplatin was completely in solution. Once the cisplatin was fully dissolved in the water, the dendrimer was added dropwise, under nitrogen, and stirred over a period of 45 minutes. The solution was isolated from light and stirred under nitrogen at room temperature for a reaction time of 24 hours. The unreacted or excess cisplatin was removed using Centricon Plus-80 MWCO 5000 (Millipore, Bioseparations). Upon recovery of the of retentate, the isolated solution was lyophilized for 48 hours (The Labconco FreeZone 4.5 Lit.) to give the hygroscopic dendrimer-platinate encapsulate as a fine while powder.

Results

The weight percent was determined at 19.25, 16.82, 16.81 wt % Pt for the 3.5, 4.5, and 5.5 poly(amidoamine) generation dendrimers, respectively. The data appears to suggest that the increased generations slightly lowers the rate of platin loading in the dendrimer-platin conjugates because of the compact (physical crowding) surface groups. However, even with the use of a poly(amidoamine) dendrimer of generation 5.5 with sodium carboxylate surface groups, a loading of 16.81 wt % Pt is obtained. Considering the molecular weight of the PAMAM dendrimers (generation 3.5, MW 12931; 4.5, MW 26252; and 5.5, MW 52913), the weight percent in terms of molar ratio indicates an increased uptake of platin from lower to higher generations.

Example 7

Kinetic Study of Reaction Procedure

Method

Reactions were carried out where a poly(amidoamine) Starburst® dendrimer of generation 3.5 with sodium carboxylate surface groups were dissolved in 20 ml of 18Ω water (Barnstead-Nanopure) and reacted with cisplatin at a molar ration of 32:1. The cisplatin was dissolved in 300 ml of 18Ω water (Barnstead-Nanopure) and gently heated (35° C.) until the cisplatin was completely in solution. Once the cisplatin was fully dissolved in the water, the dendrimer was added dropwise, under nitrogen, and stirred over a period of 45 minutes. The solution was isolated from light and stirred under nitrogen at room temperature for reaction times of 4 hours, 24 hours, and 48 hours. The unreacted or excess cisplatin was removed using Centricon Plus-80 MWCO 5000 (Millipore, Bioseparations). Upon recovery of the retentate, the isolated solution was lyophilized for 48 hours (The Labconco FreeZone 4.5 Lit.) to give the hygroscopic dendrimer-platinate encapsulate as a fine white powder.

Results

The weight percent was determined at 5.81, 19.25, 20.26 wt % Pt for the reaction times of 4, 24 and 48 hours, respectively. The data appears to suggest that the longer reaction times (i.e., 24 hours versus 4 hours) favors a higher platin loading in the dendrimer-platin conjugates. However, when the reaction time was increased to 48 hours, platin loading remained essentially unchanged. This indicates that the optimum loading is reached using a 24 hour reaction time.

Example 8

Chloride Ion Release

Method

Figure 9:
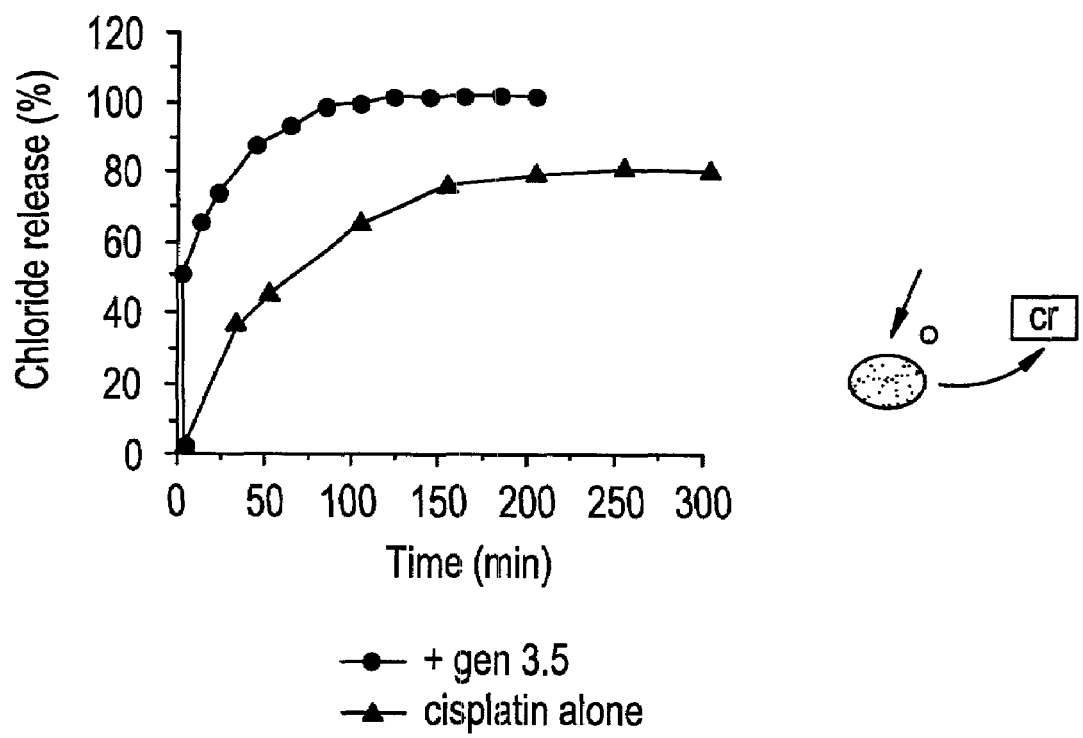
FIG. 9 is a graph showing chloride release from cisplatin in water and during reaction of cisplatin to a generation 3.5 polyamidoamine.

A chloride ion release meter (Jenway) was used to determine the reaction kinetics of the cisplatin and dendrimer reaction. A known amount of cisplatin was reacted with a known amount of dendrimer and at specific time intervals; 20 μl of the reaction mixture was removed and added to the chloride meter and the chloride content determined. This may be an indication that the chloride ions are leaving the cisplatin on reaction with the dendrimer or hydrolysis in water. A water control was also completed. The results are shown in FIG. 9.

Result

The reaction time was found to be 4 hours. The reaction kinetics of the cisplatin and dendrimer were much faster than hydrolysis alone.

Example 9

Atomic Absorption Spectroscopy

Method

A known amount of dendrimer-platinate (typically 10 mg) was dissolved in DDW (250 ml), and standards of cisplatin or potassium tetrachloroplatinate (II) were made up in the ppm range 1–100. A few drops of concentrated nitric acid (1.0 M (BDH)) were added to prevent interference. A Perkin-Etmer atomic absorption spectrophotometer was used. The machine was set at the maximum PPM and calibrated on the PPM range. The dendrimer-platinate (unknown) was then analyzed and a calibration curve constructed. The content of platinum was assessed and expressed as a weight percentage.

Result

Typically the dendrimer-platinate (cisplatin) contained 25 wt % platinum.

Example 10

NMR, GPC and PCS.

Method

Samples of dendrimer-platinate were analyzed using NMR (Bruker 400 MHz) using 1H, 13C, HCOSY, HCCOSY. GPC was used to analyze the sample on G2000 and G4000PW columns (Supelco) linked in series with refractometer (RI (Gilson)) and UV-Vis spectrophotometer detection (Severn). The pump flow rate was set to 1 ml/min. The RI range was typically set to 2–4 AU, and the UV-Vis detection wavelength was set to the UV absorbance of dendrimer-platinate solution (279 nm). The mobile phase used were water, PBS and high salt (0.25 NaCl). The columns were calibrated using pullulan and protein standards. Dendrimer generation 3.5 and dendrimer-platinate were analyzed by PCS in DDW.

Result

The NMR suggests surface conjugation of the platinate on the dendrimer, through chemical shift enhancements in key resonances relating to carboxy groups. The GPC showed the presence of a number of species which appeared to be dendrimer affragate complex with platinum, with potentially the presence of mono- and dimeric-dendrimers as well. The particle size for the dendrimer was approximately 4 nm and the dendrimer-platinate 44 nm. Several possible modes of platinum binding to dendrimer are shown in FIG. 10.

Example 11

Modification of Surface Functionalities

Method

Poly(amidoamine) Starburst® dendrimers of generation 3.5 with varying surface groups dissolved in 20 ml of 18Ω water (Barnstead-Nanopure) were reacted with cisplatin. A molar ratio of cisplatin to dendrimer of 32:1, 16:1, 32:1, respectively, was used and surface groups consisted of amine groups, acetamide groups, and extended carboxylic groups, respectively. The extended carboxylic groups were prepared by reacting the generation 3 amine groups with succinic anhydride in DMSO. This involved the formation of an amide group on the surface amine (e.g., from methylmethacrylate) with a concurrent ring opening of the succinic anhydride to produce extended carboxylic acid groups (e.g., carboxylated surface). The cisplatin was dissolved in 300 ml of 18Ω water (Barnstead-Nanopure) and gently heated (35° C.) until the cisplatin was completely in solution. Once the cisplatin was fully dissolved in the water, the dendrimer was added dropwise, under nitrogen, and stirred over a period of 45 minutes. The solution was isolated from light and stirred under nitrogen at room temperature for a reaction time of 24 hours. The unreacted or excess cisplatin was removed using Centricon Plus-80 MWCO 5000 (Millipore, Bioseparations). Upon recovery of the of retentate, the isolated solution was lyophilized for 48 hours (The Labconco FreeZone 4.5 Lit.) to give the hygroscopic dendrimer-platinate encapsulate as a fine white powder.

Results

These conjugates resulted in very low platin loading, 6.25, 0.98, and, 0.01 wt % Pt respectively. These data suggest that the first interior amine groups, as well as the acrylate derived carboxylate groups on the surface of the dendrimer may play a significant role in the uptake of the platinate.

Example 12

Purification and Reproducibility

Method

The reaction of cisplatin with dendrimers appears to still contain unbound cisplatin, even after several hours reaction time. Therefore, as a part of the synthetic procedure in the preparation of dendrimer-platinates the unbound cisplatin must be removed. Operating on the general premise that the cisplatin was covalently attached to the dendrimer a number of commercially available ultrafiltration devices were tested as a means to remove the unbound cisplatin. Specifically tested were: (1) an Amicon stirred cell with a 3000 MWCO or a 10000 MWCO membrane where fluid is forced through the membrane under nitrogen pressure, (2) Amicon Centriprep devices with 3000 MWCO filters where fluid is forced through the membrane by centrifugation, and (3) Amicon Centricon plus devices with 5000 MWCO filters where fluid is forced through the membrane by centrifugation. Theoretically, the retentate can be repeatedly washed in these devices thus continuously diluting out any remaining cisplatin. The dendrimer-cisplatin conjugates of this example were synthesized in a similar manner as those of Examples 5B through 7, and all the reaction reported used the same lot of dendrimer, the same ration of cisplatin to dendrimer, and the same reaction times.

Results

The retention of cisplatin by the dendrimer decreased with increased purification times and increased wash volumes. The results are summarized in the table below. The results indicate that the weight percent of platinum found in the final product depends on the filtration technique, as well as the volume of solvent used to wash the retentate in the purification technique. The practical significant of these data is as follows: first, the data strongly suggest that there is a significant loss of platin from the conjugate during the purification process, thereby indicating that the platin is not irreversibly or covalently bound to the dendrimer; and second, the loss of platin during filtration may roughly approximate the rate of release.

Influence on the purification technique on Pt loading of the dendrimer-platinate

| Weight of Dendrimer | Purification | Yield (wt %) | Wt % Pt |
|---|---|---|---|
| 0.0757 | 2.66 hrs, CTP3K, no wash | 74.8 | 6.96 |
| 0.1245 | 5–6 hrs, CTP3K, 93–103 ml wash | 60.7 | 3.18 |
| 0.2565 | 8 hrs, SC3K, 580 ml wash | 59.4 | 2.34 |
| 0.2285 | 22.77 hrs, SC10K, 1525 ml wash | 65.2 | 0.64 |

SC = Stirred Cell, CTP = Centiprep

It also appears from these data that a fast wash of the conjugate does remove the unbound surface Pt and perhaps also some bound surface Pt; however, a long wash will cause the encapsulated Pt to be removed from the interior of the dendrimer.

Example 13A

In vitro Release of Platinum from the Dendrimer-Platinate in Biological Fluids

Method

Known amounts of cisplatin and dendrimer were placed in two buffered solutions 25 (PBS at pH 7.4 and Citrate-Phosphate at pH 5.5) to simulate different biological compartments (the plasma/extracellular and the lysosomal compartments, respectively). The solution was sealed in a dialysis bag with a MWCO of 10 KD. Then the bag was placed in a container filled with the respective buffered solution. The solutions were then placed in heated water bath at 37° C. At regular intervals, samples from the buffer solutions were removed and analyzed in triplicate (over a period of 74 hours). At the end of the experiment, a sample was taken from within the bag. All the samples were analyzed using atomic absorption spectroscopy as described previously.

Result

The amount of platinum released at pH 5.5 was slightly greater than that released at pH 7.4. However, as shown in FIG. 11, the total amount released over time remained less than 1% of the total.

Example 13B

Cell Cytotoxicity of Dendrimer-platinate (B16F10, L1210, CorL23)

Method

Cells were seeded at a density of $1\times10^5$ cells per ml ($1\times10^4$ cells per well) in a 96 well flat bottomed microtitre plate (Costar) in RPMI 1640 tissue culture media (Gibco) supplemented with 10% FCS (Gibco). All cellular growth and cytotoxic incubations were carried out in a cell incubator at 37° C. and 5% $CO_2$ atmosphere.

Cell density was assessed using an improved neurenbrow hemocytometer (Sigma). The cells were washed with PBS twice and fresh RPMI media (supplemented with FCS) added, the cells were then seeded in a microtitre plate. The cells were left for 24 hours to recover and re-adhere. If cells were in a suspension they were spun at 1000×g and resuspended in fresh media.

Figure 12:
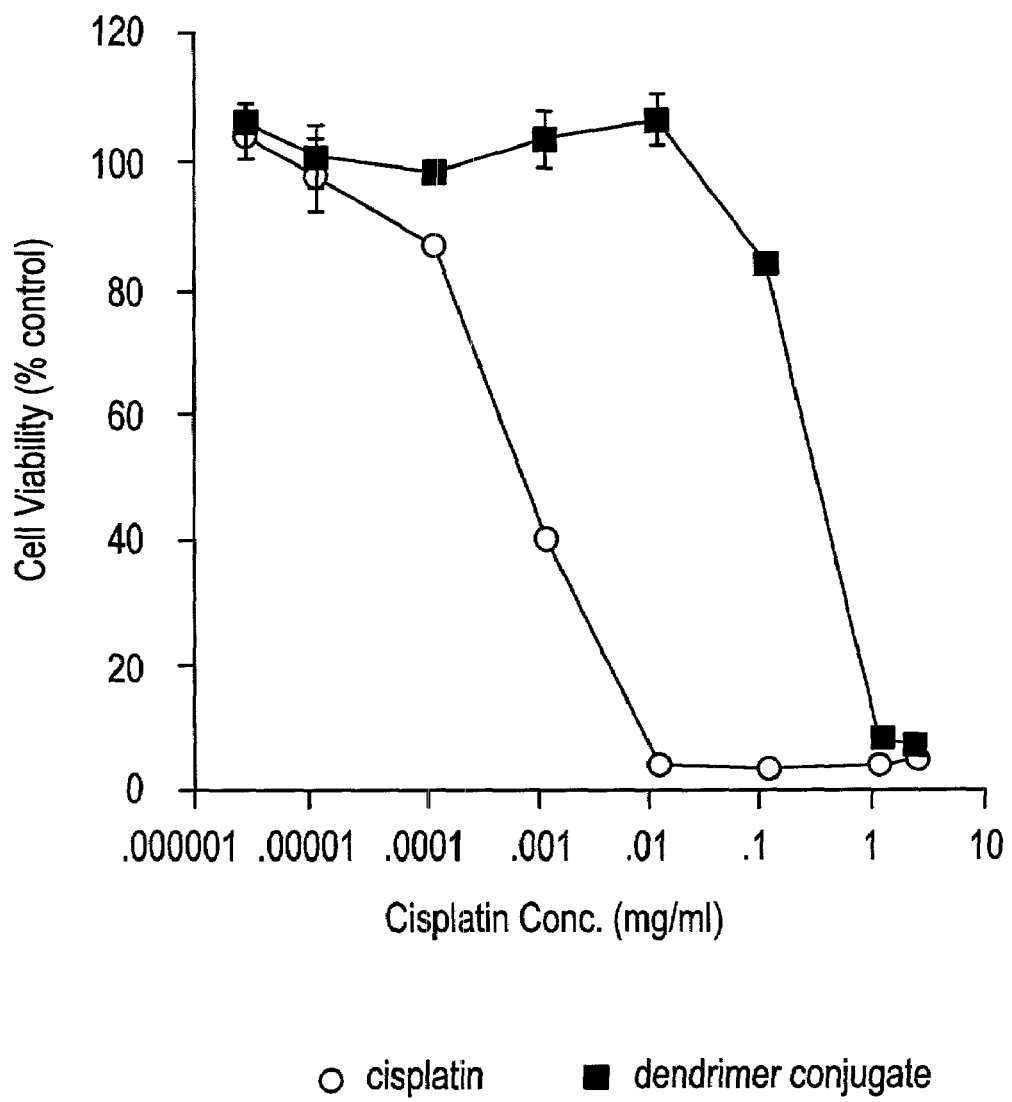
FIG. 12 is a graph showing the effect of cisplatin and dendrimer conjugate on Cor L23 cells in vitro.
Figure 13:
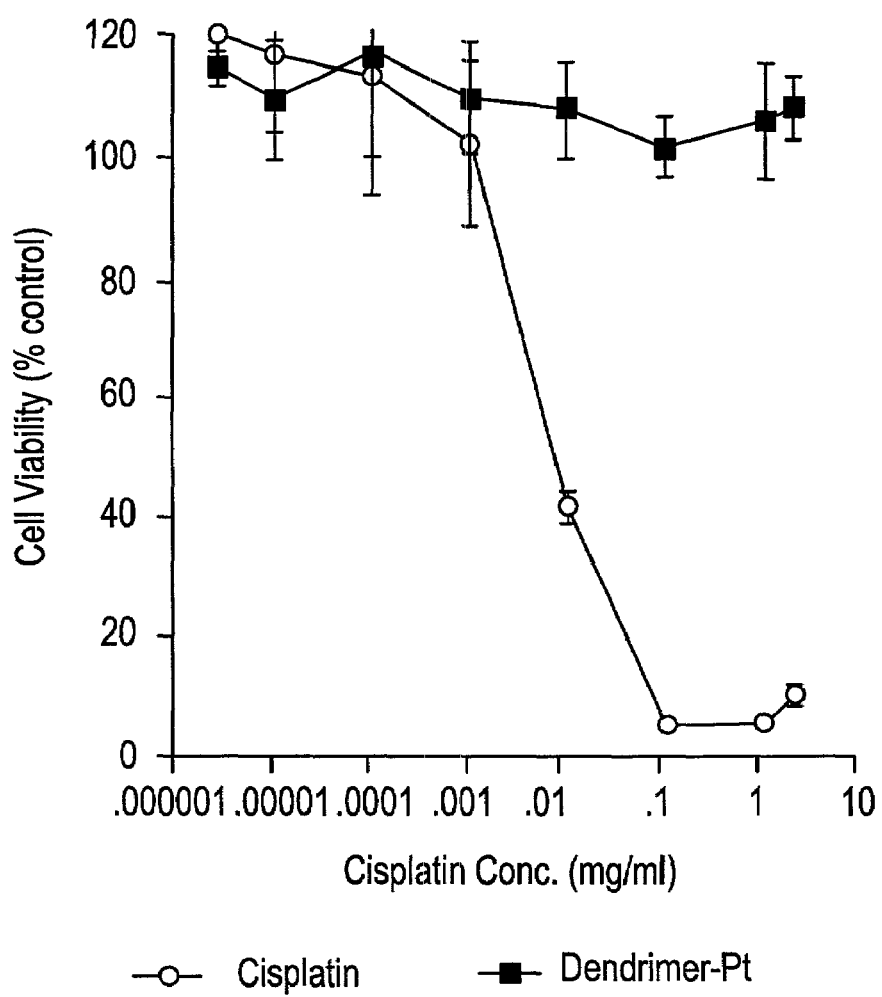
FIG. 13 is a graph showing the effect of cisplatin and dendrimer conjugate on B16F10 cells in vitro.
Figure 14:
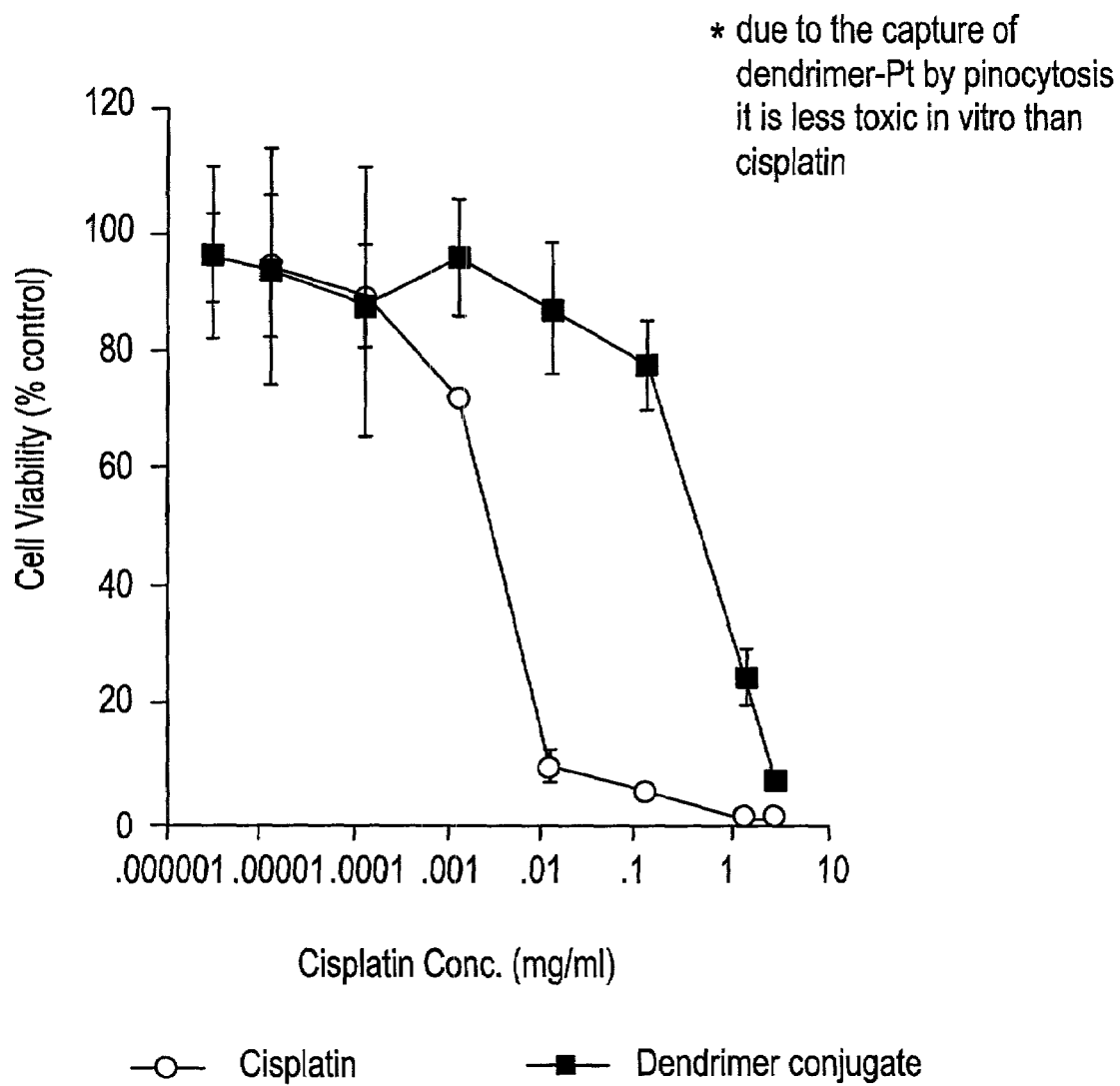
FIG. 14 is a graph showing the effect of cisplatin and dendrimer conjugate on CCRF cells in vitro.

The dendrimer-platinate and cisplatin were dissolved in RPMI media (supplemented with FCS) and then sterilized through a 0.2 μm sterile filter (Acrodisk), the first few microliters of the solution being discarded in the case of adherence of the polymer to the filter membrane. Then dendrimer and cisplatin were added in increasing concentrations to the cells in the microtitre plate. Some cells were left in media only to act as cellular controls. The cells were left in the incubator for 72 hours, and checked occasionally for yeast or bacterial contamination. Five hours prior to the incubation time end point, at 67 hours, 20 μl of MTT was added and the cells left for the final 5 hours. Then cellular media was removed and 100 μl of optical grade DMSO (Sigma) was added and the MTT crystals dissolved. The plates were read in a Titerteck plate reader and the results (OD) are expressed in FIGS. 12, 13 and 14 as a percentage of the OD seen in cell wells containing no dendrimer-platinate or cisplatin.

Result

The dendrimer-platinate was less cytotoxic than the cisplatin alone by several orders of magnitude.

Example 14

Pharmacology (I.P. Tumor Verses I.P. Injection)

Method

Li 210 or B16F10 cells were injected at a cell density into a mouse (DBA2 or C57 respectively, 25 g) at a cell density of $1\times10^5$ (0.9% saline solution) into the intraperitoneal (I.P. 100 μl) cavity. Twenty-four hours later, the dendrimer-platinate and cisplatin (on one day or on three consecutive days) were injected at a concentration according to the weight of the mouse (e.g. 1 mg/kg–15 mg/kg). The mouse body weight and general toxicity was also monitored according to UK guidelines in the use of animals used in neoplasia studies. At the end point the gross morphology of the organs was noted.

Result

Figure 15:
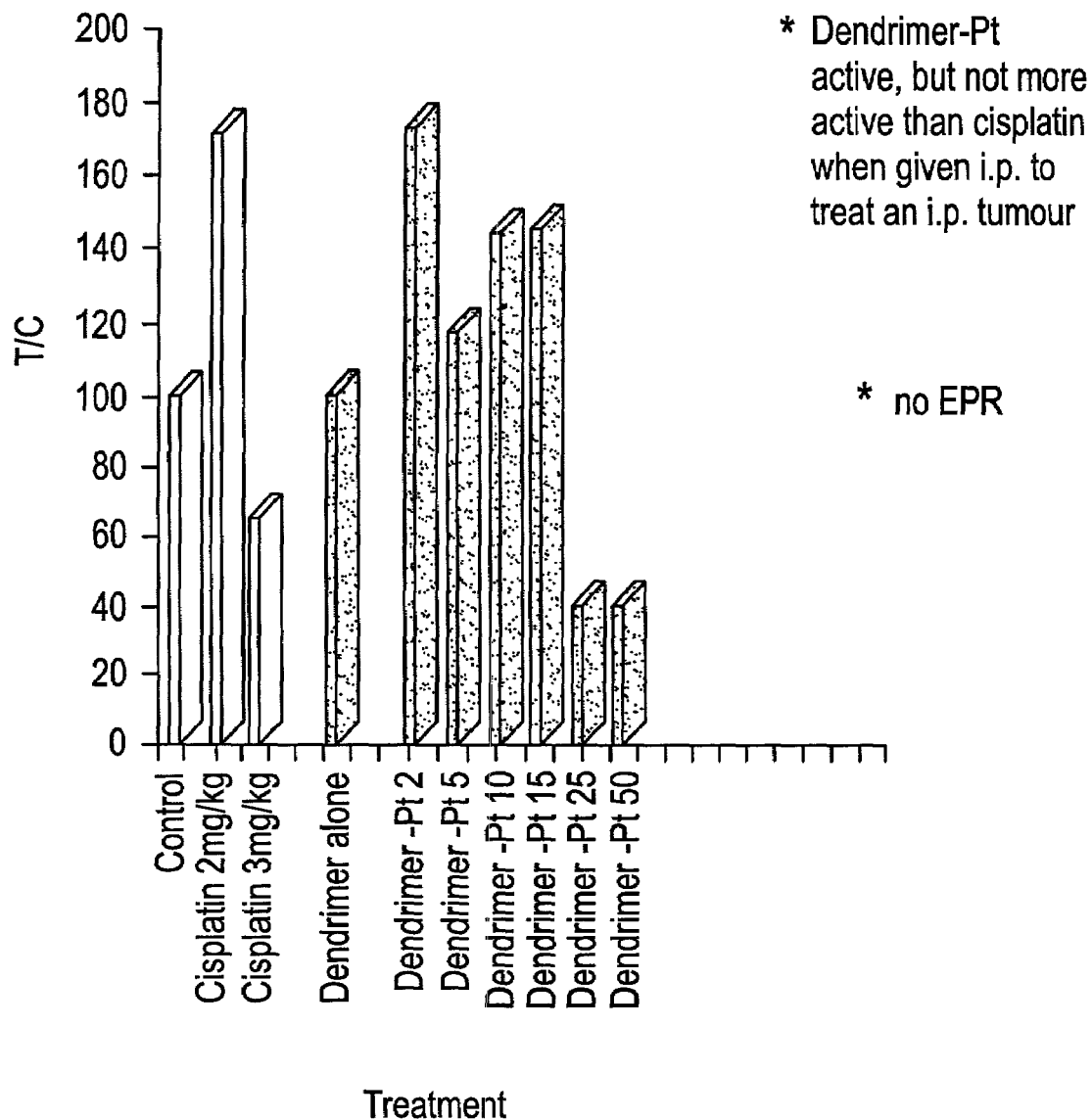
FIG. 15 is a bar graph showing the effect of intraperitoneal injection of dendrimer-platinum conjugate treatment on intraperitoneally injected tumors.

This pharmacology demonstrated the maximum tolerated does of the dendrimer-platinate (25–50 mg/kg). As shown in FIG. 15, I.P. delivery of dendrimer platinate showed anti-tumor activity but not substantially better than cisplatin alone.

Example 15

Pharmacology (S.C. Tumor Verses I.V. Injection)

Method

B16F10 cells were injected at a cell density of $1\times10^5$ (0.9% saline solution) into the left or right flank of the C57 mouse S.C. The mouse was then left until the tumor was visible at a palpable size of between 50–100 mm². Then the dendrimer-platinate and cisplatin were injected I.V. into the tail vein at the respective doses. The animal was monitored and the tumor size measured using calipers and recorded on a daily basis. When the animal tumor size was between 300–400 mm², the animal was culled. The tumor excised and weighed and gross morphology of the organs noted.

Result

Figure 16:
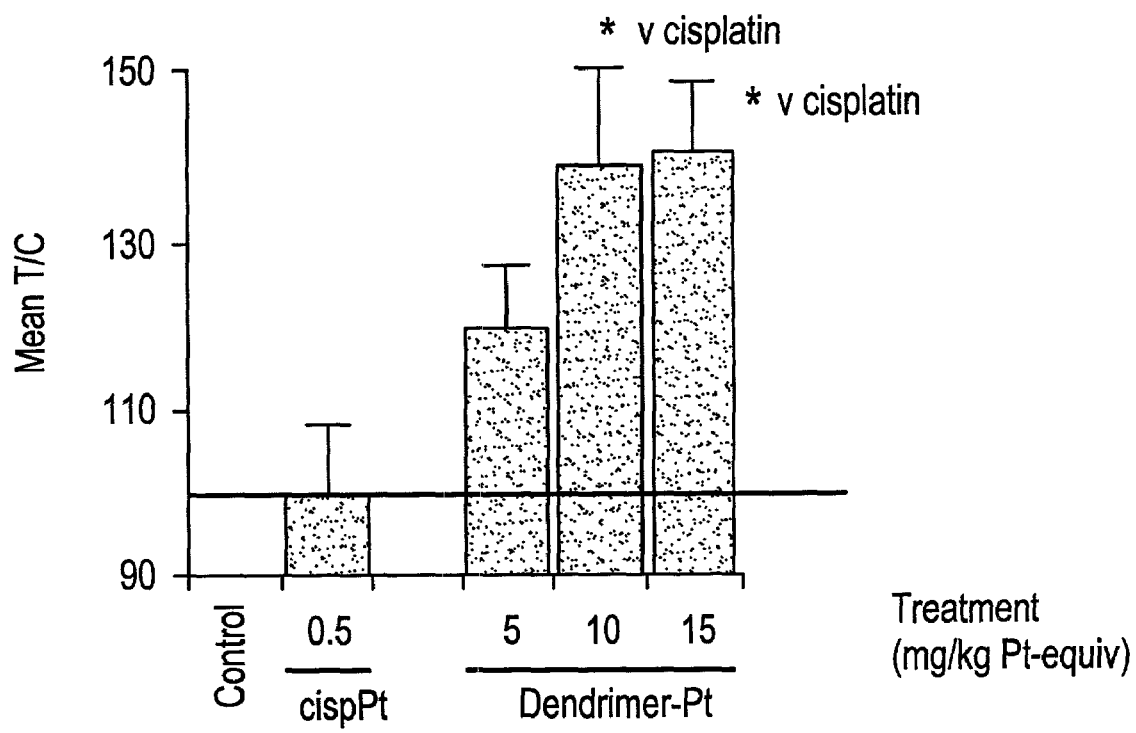
FIG. 16 is a bar graph showing the effect of dendrimer-platinum conjugate on established B16 melanoma.

The dendrimer-platinate was active against the S.C. tumor and demonstrated a significant difference in the final tumor weight and survival time, as shown in FIG. 16.

Example 16

Biodistribution of Dendrimer-platinate in vivo

Method

C57 mice were injected S.C. with B16F10 cells at a cell density of $1\times10^5$ cells per mouse. The tumor was allowed to reach a palpable size before injecting the dendrimer-platinate or cisplatin I.V. At specific time points (0–24 hours) the animal was culled and key organs (liver, kidney, and blood) including the tumor were isolated and weighed. The organs were solubilized in concentrated nitric acid (10M) and hydrogen peroxide added to decolorize the solution during boiling. The solutions were made up to a fixed volume (25 ml) and then analyzed using AAS after addition of lanthanum (La) (excess) to free up bound platinum (Pt).

Result

Figure 17:
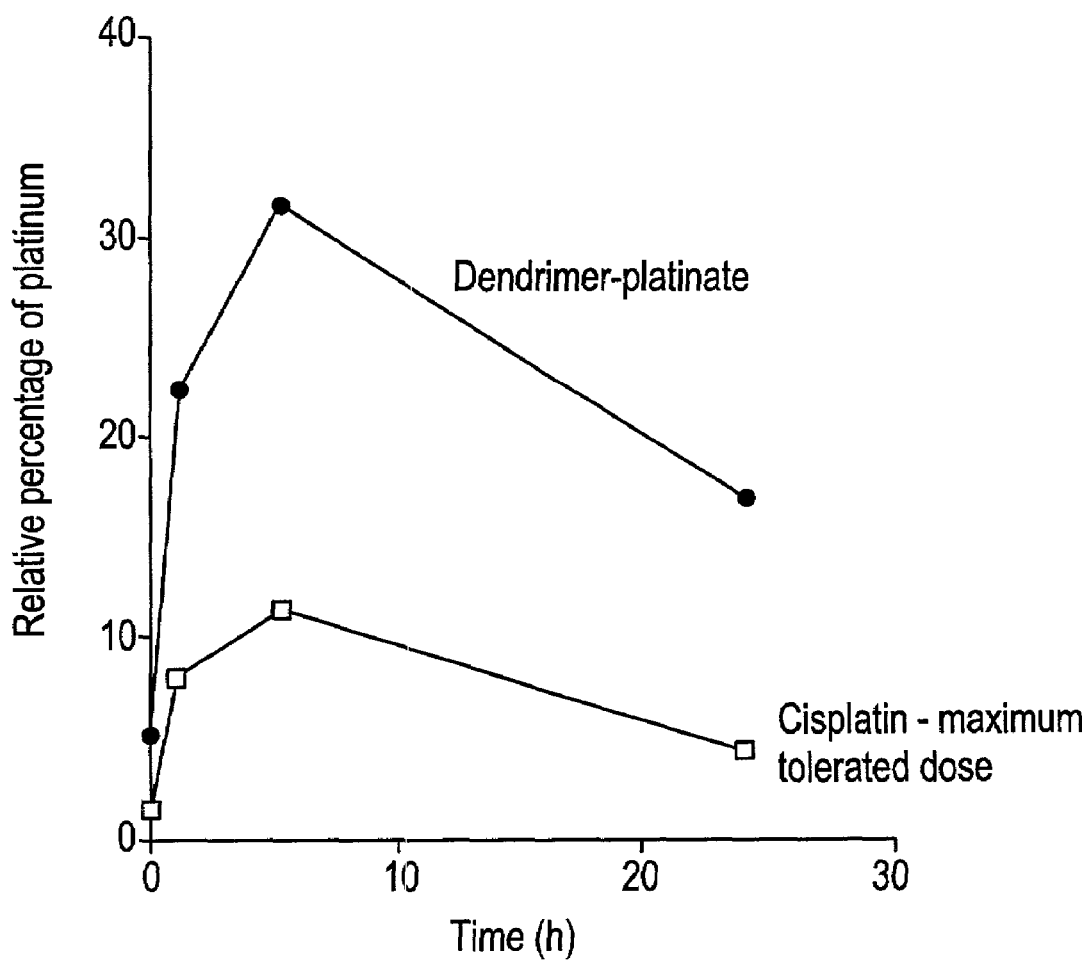
FIG. 17 is a graph showing the accumulation of dendrimer-platinum and platinum intravenously injected in C57 mice bearing B 16F10 subcutaneously implanted tumor.

Compared to cisplatin alone, the dendrimer-cisplatin was found to accumulate preferentially in the tumor by at least 3x, relatively quickly after the injection. The results are shown in FIG. 17.

Example 17

Measurement of the Pharmracokinetics of Cisplatin and Dendrimer-platinate in vivo Method B16F10 cells ($10^5$ cells) were injected into C57 mice S.C. to provide a solid tumor model. When the tumor developed to a mean area of 50–100 mm² (after approximately 12 days) animals were injected I.V. with a single dose of cisplatin (1.0 mg/kg, at is maximum tolerated dose) or dendrimer-Pt (1 or 15 mg/kg). In both cases animals were monitored for general health and weight loss. At time points 0, 1, 5, 12, 24 and 48 hours mice (5 per group) were culled. Blood and tissue samples were taken. The organs were digested in nitric acid (10 ml, 10M) under heating (boiling for 2 days). Hydrogen peroxide was added to a known volume to oxidize the solution and the Pt concentration determined by graphite AAS.

Result

The tumor AUC for accumulation of dendrimer platinate was 5 fold (dendrimer-Pt 1 mg/kg) and 50 fold (dendrimer-Pt 15 mg/kg) higher than seen for cisplatin (1 mg/kg). Accumulation at sites of toxicity (kidney) were reduced.

Summary of Body Distribution Data

| | AUC value (µg Pt/mL blood or µg Pt/organ) over 48 h | | |
|---|---|---|---|
| Organ | Cisplatin 1 mg/kg | Dendrimer-Pt 1 mg/kg | Dendrimer-Pt 15 mg/kg |
| Tumor | 5.3 | 25.4 | 264.9 |
| Blood | 9.4 | 10.7 | 502.0 |
| Liver | 51.6 | 17.0 | 193.2 |
| Kidney | 57.6 | 138.1 | 244.2 |

Ratio of AUC Values

| Organ | Ratio AUG Dendrimer-Pt (1 mg/kg)/AUG Cisplatin (1 mg/kg) | Ratio AUG Dendrimer-Pt (15 mg/kg)/AUG Cisplatin (1 mg/kg) |
|---|---|---|
| Tumor | 4.8 | 50.0 |
| Blood | 1.1 | 53.4 |
| Kidney | 2.4 | 4.2 |
| Liver | 0.3 | 3.7 |

Ratio of AUC values obtained in terms of Tumor/Blood, Tumor/Liver or Tumor/Kidney

| Ratio | Cisplatin (1 mg/kg) | Dendrimer-Pt (1 mg/kg)) | Dendrimer-Pt (15 mg/kg) |
|---|---|---|---|
| Tumor/Blood | 0.56 | 2.37 (4x) | 0.53 (same) |
| Tumor/Kidney | 0.09 | 0.18 (2x) | 1.08 (12x) |
| Tumor/Liver | 0.10 | 1.49 (15x) | 1.37 (14x) |

Results and Discussion

Dendrimer-Pt The cisplatin and carboplatin used in these examples interacted with the carboxy surface of generation 3.5 PAMAM and as a result was associated with the dendrimer giving a conjugate with approximately 20 to 25 wt % Pt loading which was highly water soluble and stable on storage. Lack of interaction of Pt with dendrimer generation 4 indicates that Pt does not become entrapped or chelated in the dendrimer core or react with terminal primary amino groups, without the assistance of the carboxylate terminal groups. While it is uncertain what the precise method of association between the dendrimer and the cisplatin and platin-based analogue antineoplastic agent is, and while not wishing to be bound by theory, it is believed that the advantageous results of the present invention are obtained because of at least three possibilities. First, it appears that cisplatin may covalently couple to the carboxylate groups on the surface of the dendrimer. Second, it appears that the cisplatin can associate with, and perhaps be encapsulated or entrapped within the interior of the dendrimer, and, it is also possible that the dendrimer-antineoplastic conjugate of this invention results form a hybrid of these two mechanisms. IR and NMR confirmed Pt interaction at the dendrimer surface. Pt was found to be tightly bound with very little Pt release over 72 hours in vitro.

In vitro Evaluation Dendrimer generation 3.5 undergoes slight degradation in physiological buffers over 24 hours, increasing with pH (5.5–7.4), and is also degraded in strong acid.

Figure 19:
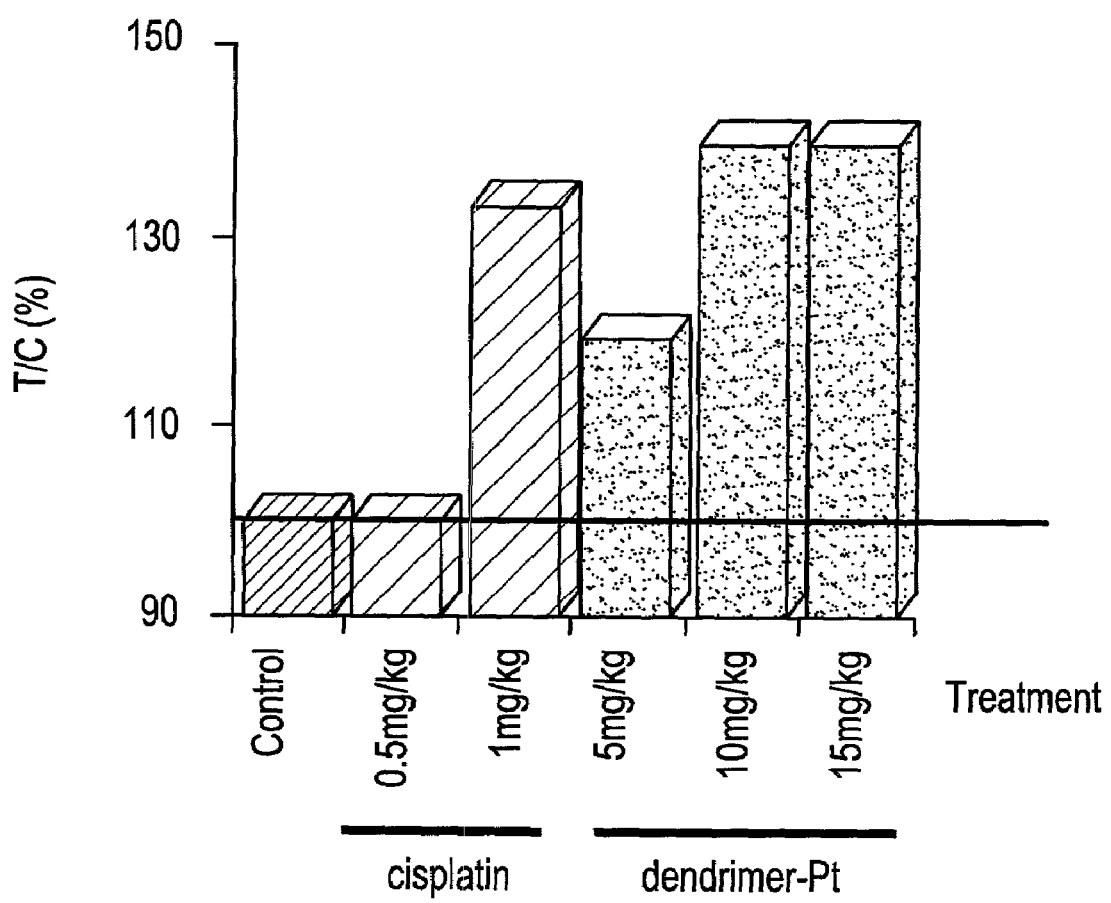
FIG. 19 is a bar graph showing the effect of dendrimer-platinum conjugates on established B16 melanoma (intravenously single dose)
Figure 20A:
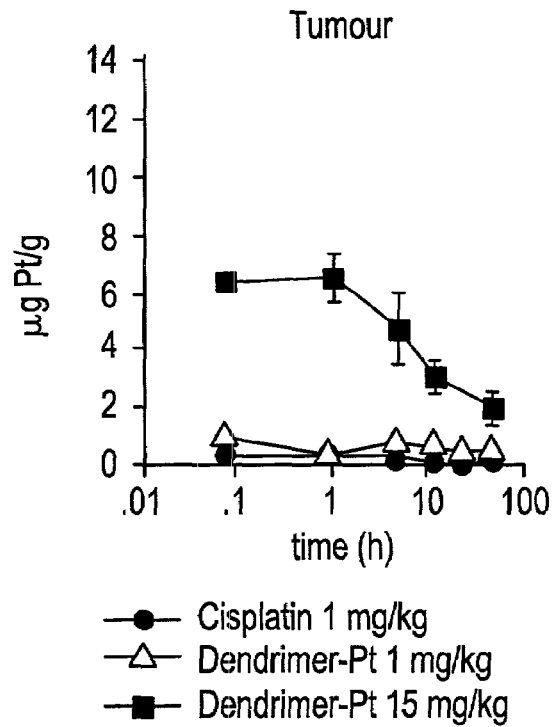
FIGS. 20A–D are a series of plots which show the 48 hours pharmacokinetics of dendrimer-Pt and cisplatin in C57 mice bearing subcutaneous (S.C.) B16F10 tumor.
Figure 20B:
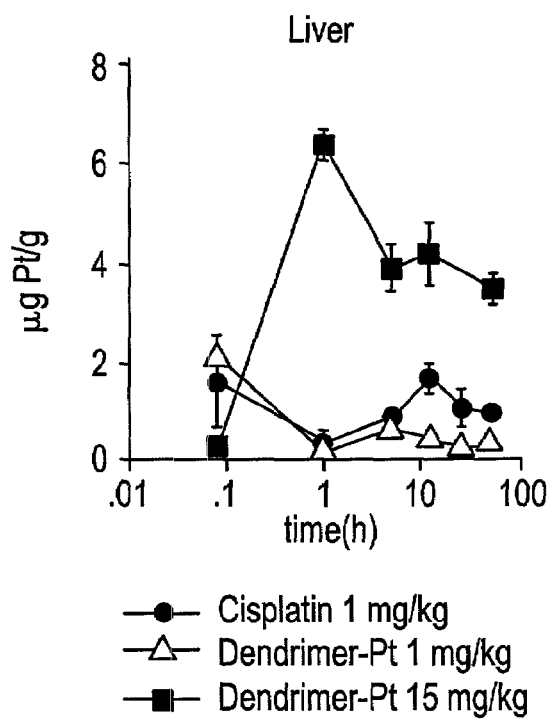
Figure 20C:
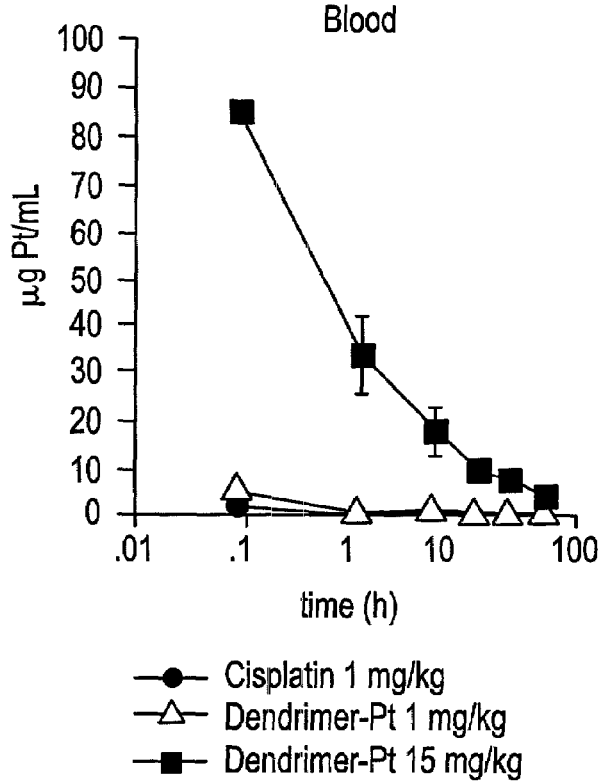
Figure 20D:
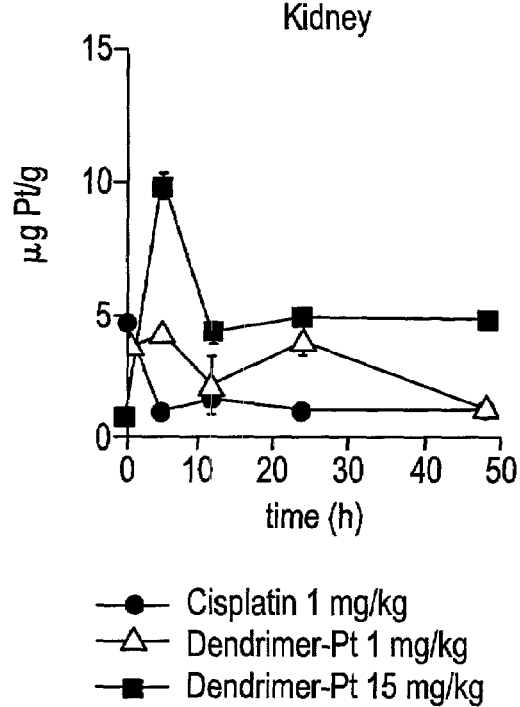

The dendrimer-Pt displayed anti-tumor activity against CCRF and Cor L23 but in both cases was less active than cisplatin; this was expected due to the different mechanism of cellular uptake. Up to concentrations of 2 mg/ml (Pt-equiv.) the dendrimer-Pt was inactive against B16F10 melanoma in vitro (see FIG. 19).

| | $IC_{50}$ Values ($\mu$g/ml, Pt-equiv.) | |
|---|---|---|
| Cell Line | Cisplatin | Dendrimer-Pt |
| B16F10 | 9 | >2000 |
| CCRF-CEM | 5 | 520 |
| Cor L23 | 1 | 380 |

Figure 18:
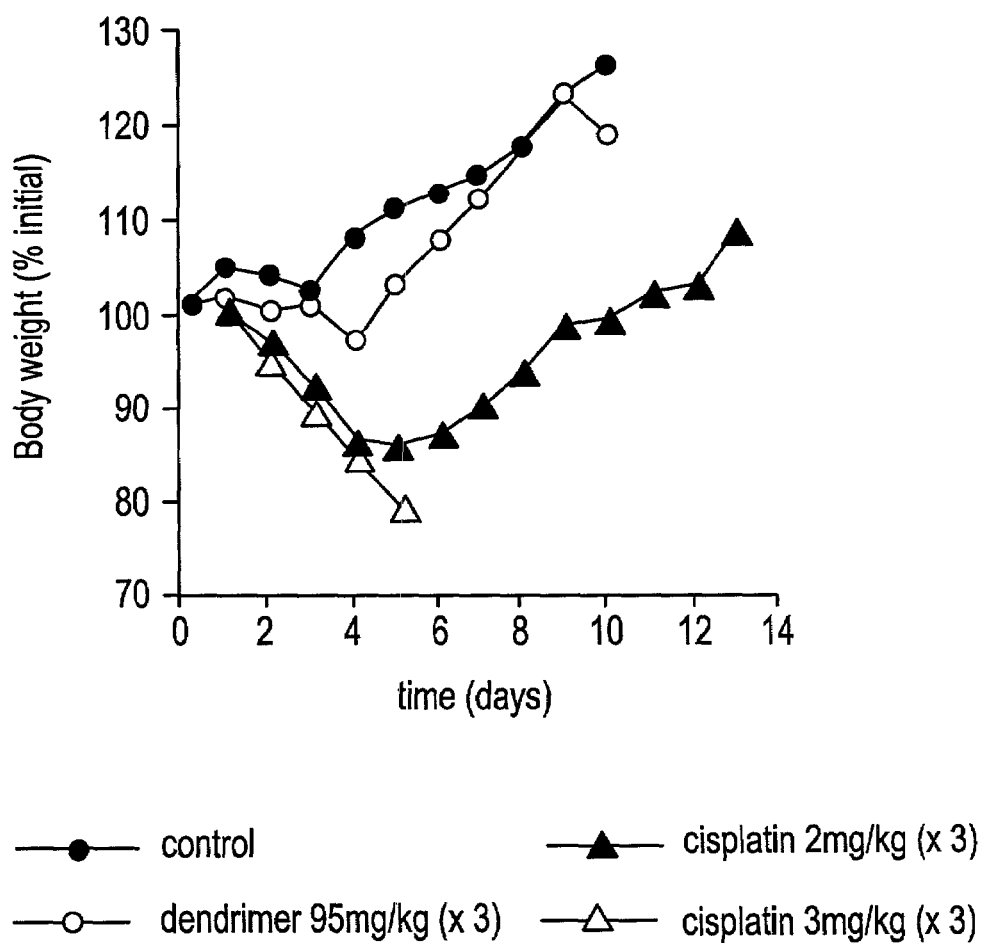
FIG. 18 is a graph showing the effect of dendrimer on the body weight of DBA2 mice bearing L1210 leukemia.

In vivo Evaluation The dendrimer-Pt showed anti-tumor activity in all the tumor models tested, including the platinum resistant B16F10 model. It was confirmed that the generation 3.5 dendrimer, without cisplatin, displayed neither inherent anti-tumor activity nor general toxicity (see FIG. 18).

| Treatment | Dose (Pt-equiv mg/Kg) | T/C | Toxic Deaths |
|---|---|---|---|
| Activity against L1210 ip (doses I.P. days 1, 2, 3) | | | |
| Cisplatin | 2 | 171 | 0/10 |
| Cisplatin | 3 | 64 | 9/10 |
| Dend-Pt | 2 | >123 | 0/5 |
| Dent-Pt | 10 | >132 | 0/5 |
| Dent-Pt | 15 | >132 | 0/5 |
| Activity against B16F10 I.P. (dose day 1) | | | |
| Cisplatin | 5 | 89 | 2/5 |
| Dend-Pt | 5 | 105 | 0/5 |
| Dend-Pt | 10 | 108 | 0/5 |
| Dend-Pt | 10 | 129 | 5/5$^T$ |

$^T$chronic toxicity

Anti-tumor activity was more pronounced against sensitive tumors, e.g. L1210, and in the case of S.C. tumors with I.V. administration of drug.

CONCLUSION

Dendrimer-Pt has greater water solubility than cisplatin, was 3–5 times less toxic, has greater anti-tumor activity in vivo and was found to preferentially accumulate in tumor tissue.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. An antineoplastic dendritic polymer conjugate, comprising:
   a dendritic polymer conjugated to an antineoplastic agent wherein the dendritic polymer is a poly(amidoamine) dendrimer having carboxylate functional groups,
   wherein the antineoplastic agent is cisplatin or carboplatin and is encapsulated within the dendritic polymer,
   wherein the percent by weight of platinum in the conjugate is at least about 16%, and
   wherein the antineoplastic dendritic polymer conjugate has a therapeutic effect on malignant tumors.

2. The antineoplastic dendritic polymer conjugate of claim 1, wherein the dendritic polymer is acrylate derived.

3. The antineoplastic dendritic polymer conjugate of claim 2, wherein the conjugate is an aggregate of poly(amidoamine)dendrimers of generation 3.5, ethylenediani-ine core, with cisplatin.

4. The antineoplastic dendritic polymer conjugate of claim 1, wherein the molar ratio of the cisplatin to dendritic polymer in the conjugate is from about 100:1 to about 1:1.

5. The antineoplastic dendritic polymer conjugate of claim 3 or 4, wherein the molar ratio of cisplatin to dendritic polymer in the conjugate is about 35:1.

6. The antineoplastic dendritic polymer conjugate of claim 1, wherein the antineoplastic agent is cisplatiin.

7. The antineoplastic dendritic polymer conjugate of claim 1, wherein the poly(aniidoamine)dendrimer is a generation from 3.5 to 7.5.

* * * * *